United States Patent
Wang et al.

(10) Patent No.: US 7,790,015 B2
(45) Date of Patent: *Sep. 7, 2010

(54) ENDPOINT FOR ELECTROPROCESSING

(75) Inventors: Yan Wang, Sunnyvale, CA (US);
Antoine P. Manens, Mountain View, CA (US); Siew S. Neo, Santa Clara, CA (US); Alain Duboust, Sunnyvale, CA (US); Liang-Yuh Chen, Foster City, CA (US)

(73) Assignee: Applied Materials, Inc., Santa Clara, CA (US)

( * ) Notice: Subject to any disclaimer, the term of this patent is extended or adjusted under 35 U.S.C. 154(b) by 336 days.

This patent is subject to a terminal disclaimer.

(21) Appl. No.: 11/930,495

(22) Filed: Oct. 31, 2007

(65) Prior Publication Data

US 2008/0051009 A1 Feb. 28, 2008

Related U.S. Application Data

(63) Continuation of application No. 10/949,160, filed on Sep. 24, 2004, now abandoned, which is a continuation-in-part of application No. 10/456,851, filed on Jun. 6, 2003, now Pat. No. 7,112,270, which is a continuation-in-part of application No. 10/244,688, filed on Sep. 16, 2002, now Pat. No. 6,848,970, and a continuation-in-part of application No. 10/391,324, filed on Mar. 18, 2003, now abandoned.

(51) Int. Cl.
*B23H 3/02* (2006.01)
*C25F 7/00* (2006.01)
(52) U.S. Cl. ........................ 205/644; 205/641; 204/228.7
(58) Field of Classification Search ................ 205/641, 205/644; 204/228.7
See application file for complete search history.

(56) References Cited

U.S. PATENT DOCUMENTS

| | | | |
|---|---|---|---|
| 3,162,588 A | 12/1964 | Bell |
| 3,448,023 A | 6/1969 | Bell |
| 3,873,512 A | 3/1975 | Latanision |
| 4,119,515 A | 10/1978 | Costakis |

(Continued)

FOREIGN PATENT DOCUMENTS

DE 3413762 A1 5/1983

(Continued)

OTHER PUBLICATIONS

Taiwan Office Action dated Apr. 22, 2009 for Application No. 94129144.

(Continued)

*Primary Examiner*—Harry D. Wilkins, III
*Assistant Examiner*—Nicholas A. Smith
(74) *Attorney, Agent, or Firm*—Patterson & Sheridan, LLP

(57) ABSTRACT

Method for process control of electro-processes is provided. In one embodiment, the method includes processing a conductive layer formed on a wafer using a target endpoint, detecting breakthrough of the conductive layer to expose portions of an underlying layer, and adjusting the target endpoint in response to the detected breakthrough. In another embodiment, the target endpoint is adjusted relative to an amount of underlying layer exposed through the conductive layer.

15 Claims, 13 Drawing Sheets

U.S. PATENT DOCUMENTS

| | | | |
|---|---|---|---|
| 4,125,444 A | 11/1978 | Inoue | |
| 4,713,149 A | 12/1987 | Hoshino | |
| 4,793,895 A | 12/1988 | Kaanta et al. | |
| 4,839,993 A | 6/1989 | Masuko et al. | |
| 4,934,102 A | 6/1990 | Leach et al. | |
| 4,954,141 A | 9/1990 | Takiyama et al. | |
| 4,956,056 A | 9/1990 | Zubatova et al. | |
| 5,096,550 A | 3/1992 | Mayer et al. | |
| 5,136,817 A | 8/1992 | Tabata et al. | |
| 5,217,586 A | 6/1993 | Datta et al. | |
| 5,225,034 A | 7/1993 | Yu et al. | |
| 5,534,106 A | 7/1996 | Cote et al. | |
| 5,543,032 A | 8/1996 | Datta et al. | |
| 5,567,300 A | 10/1996 | Datta et al. | |
| 5,575,706 A | 11/1996 | Tsai et al. | |
| 5,578,362 A | 11/1996 | Reinhardt et al. | |
| 5,624,300 A | 4/1997 | Kishii et al. | |
| 5,637,031 A | 6/1997 | Chen | |
| 5,738,574 A | 4/1998 | Tolles et al. | |
| 5,766,446 A | 6/1998 | Spindt et al. | |
| 5,804,507 A | 9/1998 | Perlov et al. | |
| 5,807,165 A | 9/1998 | Uzoh et al. | |
| 5,846,882 A | 12/1998 | Birang | |
| 5,871,392 A | 2/1999 | Meikle et al. | |
| 5,893,796 A | 4/1999 | Birang et al. | |
| 5,911,619 A | 6/1999 | Uzoh et al. | |
| 5,931,719 A | 8/1999 | Nagahara et al. | |
| 5,938,801 A | 8/1999 | Robinson | |
| 5,966,151 A | 10/1999 | Wakahara | |
| 6,001,008 A | 12/1999 | Fujimori et al. | |
| 6,004,880 A | 12/1999 | Liu et al. | |
| 6,010,395 A | 1/2000 | Nakajima | |
| 6,017,265 A | 1/2000 | Cook et al. | |
| 6,020,264 A | 2/2000 | Lustig et al. | |
| 6,024,630 A | 2/2000 | Shendon et al. | |
| 6,051,116 A | 4/2000 | Ichinose et al. | |
| 6,056,851 A | 5/2000 | Hsieh et al. | |
| 6,066,030 A | 5/2000 | Uzoh | |
| 6,068,818 A | 5/2000 | Ackley et al. | |
| 6,090,239 A | 7/2000 | Liu et al. | |
| 6,103,096 A | 8/2000 | Datta et al. | |
| 6,116,998 A | 9/2000 | Damgaard et al. | |
| 6,141,027 A | 10/2000 | Akutsu et al. | |
| 6,153,043 A | 11/2000 | Edelstein et al. | |
| 6,156,124 A | 12/2000 | Tobin | |
| 6,159,079 A | 12/2000 | Zuniga et al. | |
| 6,171,467 B1 | 1/2001 | Weihs et al. | |
| 6,176,992 B1 | 1/2001 | Talieh | |
| 6,210,257 B1 | 4/2001 | Carlson | |
| 6,234,870 B1 | 5/2001 | Uzoh et al. | |
| 6,238,271 B1 | 5/2001 | Cesna | |
| 6,244,935 B1 | 6/2001 | Birang et al. | |
| 6,248,222 B1 | 6/2001 | Wang | |
| 6,273,798 B1 | 8/2001 | Berman | |
| 6,297,159 B1 | 10/2001 | Paton | |
| 6,319,420 B1 | 11/2001 | Dow | |
| 6,328,872 B1 | 12/2001 | Talieh et al. | |
| 6,346,482 B2 | 2/2002 | Matsumoto et al. | |
| 6,358,118 B1 | 3/2002 | Boehm et al. | |
| 6,368,184 B1 | 4/2002 | Beckage | |
| 6,368,190 B1 | 4/2002 | Easter et al. | |
| 6,379,223 B1 | 4/2002 | Sun et al. | |
| 6,381,169 B1 | 4/2002 | Bocian et al. | |
| 6,386,956 B1 | 5/2002 | Sato et al. | |
| 6,391,166 B1 | 5/2002 | Wang | |
| 6,395,152 B1 | 5/2002 | Wang | |
| 6,402,591 B1 | 6/2002 | Thornton | |
| 6,406,363 B1 | 6/2002 | Xu et al. | |
| 6,409,903 B1 | 6/2002 | Chung et al. | |
| 6,409,904 B1 | 6/2002 | Uzoh et al. | |
| 6,413,388 B1 | 7/2002 | Uzoh et al. | |
| 6,413,403 B1 | 7/2002 | Lindquist et al. | |
| 6,440,295 B1 | 8/2002 | Wang | |
| 6,447,668 B1 | 9/2002 | Wang | |
| 6,471,847 B2 | 10/2002 | Talieh et al. | |
| 6,482,307 B2 | 11/2002 | Ashjaee et al. | |
| 6,497,800 B1 | 12/2002 | Talieh et al. | |
| 6,515,493 B1 | 2/2003 | Adams | |
| 6,582,281 B2 | 6/2003 | Doan et al. | |
| 6,612,904 B1 | 9/2003 | Boehm et al. | |
| 6,630,059 B1 | 10/2003 | Uzoh et al. | |
| 6,638,863 B2 | 10/2003 | Wang et al. | |
| 6,693,036 B1 | 2/2004 | Nogami et al. | |
| 6,709,565 B2 | 3/2004 | Mayer et al. | |
| 6,726,823 B1 | 4/2004 | Wang et al. | |
| 6,736,952 B2 | 5/2004 | Emesh et al. | |
| 6,752,916 B1 | 6/2004 | Fang et al. | |
| 6,776,693 B2 | 8/2004 | Duboust et al. | |
| 6,811,680 B2 | 11/2004 | Chen et al. | |
| 6,837,983 B2 | 1/2005 | Duboust et al. | |
| 6,848,970 B2 | 2/2005 | Manens et al. | |
| 6,863,797 B2 | 3/2005 | Sun et al. | |
| 6,899,804 B2 | 5/2005 | Duboust et al. | |
| 7,066,800 B2 | 6/2006 | Chen et al. | |
| 7,070,475 B2 | 7/2006 | Manens | |
| 7,112,270 B2 | 9/2006 | Manens et al. | |
| 7,156,975 B2 * | 1/2007 | Sato et al. | 205/644 |
| 7,294,038 B2 | 11/2007 | Manens | |
| 2001/0005667 A1 | 6/2001 | Tolles et al. | |
| 2001/0024878 A1 | 9/2001 | Nakamura | |
| 2001/0027018 A1 | 10/2001 | Molnar | |
| 2001/0035354 A1 | 11/2001 | Ashjaee et al. | |
| 2001/0036746 A1 | 11/2001 | Sato et al. | |
| 2001/0040100 A1 | 11/2001 | Wang | |
| 2001/0042690 A1 | 11/2001 | Talieh | |
| 2002/0008036 A1 | 1/2002 | Wang | |
| 2002/0011417 A1 | 1/2002 | Talieh et al. | |
| 2002/0020621 A1 | 2/2002 | Uzoh et al. | |
| 2002/0025760 A1 | 2/2002 | Lee et al. | |
| 2002/0025763 A1 | 2/2002 | Lee | |
| 2002/0052126 A1 | 5/2002 | Lee et al. | |
| 2002/0070126 A1 | 6/2002 | Sato et al. | |
| 2002/0077037 A1 | 6/2002 | Tietz | |
| 2002/0088715 A1 | 7/2002 | Talieh et al. | |
| 2002/0108861 A1 | 8/2002 | Emesh et al. | |
| 2002/0130049 A1 | 9/2002 | Chen et al. | |
| 2003/0104762 A1 | 6/2003 | Sato et al. | |
| 2003/0109198 A1 | 6/2003 | Lee | |
| 2003/0114087 A1 | 6/2003 | Duboust et al. | |
| 2003/0116446 A1 | 6/2003 | Duboust et al. | |
| 2003/0213703 A1 | 11/2003 | Wang et al. | |
| 2004/0023610 A1 | 2/2004 | Hu et al. | |
| 2004/0182721 A1 | 9/2004 | Manens et al. | |
| 2005/0061674 A1 | 3/2005 | Wang et al. | |
| 2005/0121141 A1 | 6/2005 | Manens | |
| 2006/0237330 A1 | 10/2006 | Manens | |

FOREIGN PATENT DOCUMENTS

| | | |
|---|---|---|
| EP | 0 325 753 | 8/1989 |
| EP | 0 455 455 | 6/1991 |
| EP | 1 103 346 A2 | 5/2001 |
| EP | 1120694 | 8/2001 |
| GB | 2 214 520 A | 9/1989 |
| JP | 10-16213 | 1/1998 |
| JP | 2870537 | 1/1999 |
| JP | 11-042554 | 2/1999 |
| JP | 2000218513 | 8/2000 |
| JP | 2001-77117 | 3/2001 |
| JP | 2001244223 | 9/2001 |
| WO | WO 98/49723 | 11/1998 |
| WO | WO 99/41434 | 8/1999 |
| WO | WO 99/53119 | 10/1999 |
| WO | WO 00/03426 | 1/2000 |

| | | |
|---|---|---|
| WO | WO 00/26443 | 5/2000 |
| WO | WO 2004/024394 | 5/2000 |
| WO | WO 00/33356 | 6/2000 |
| WO | WO 00/59682 | 10/2000 |
| WO | WO-01-13416 | 2/2001 |
| WO | WO 01/49452 | 7/2001 |
| WO | WO-2001-52307 | 7/2001 |
| WO | WO-2001-63018 | 8/2001 |
| WO | WO-2001-71066 | 9/2001 |
| WO | WO 01/88229 | 11/2001 |
| WO | WO-2001-88954 | 11/2001 |
| WO | WO 02/23616 | 3/2002 |
| WO | WO 02/064314 | 8/2002 |
| WO | WO 03/001581 | 1/2003 |
| WO | WO 03/061905 A | 7/2003 |
| WO | WO 03/061905 A1 | 7/2003 |

OTHER PUBLICATIONS

Robert J. Contolini, "Electrochemical Planarization of ULSI Copper" Jun. 1997, Solid State Technology, pp. 155-156, 158 and 160.

Nogami, "*An Innovation to Integrate Porous Low-K Materials and Copper*", InterConnect Japan 2001; Honeywell Seminar (Dec. 6, 2001) pp. 1-12.

International Search Report for PCT/US 02/11009 dated Feb. 25, 2003.

PCT International Search Report for PCT/US03/01760 dated May 27, 2003.

PCT International Search Report for PCT/US03/29230 dated Feb. 3, 2004.

PCT Written Opinion for PCT/US03/01760 dated Mar. 8, 2004.

PCT International Search Report dated Mar. 30, 2005 for PCT/US2004/007501.

PCT Written Opinion dated Mar. 30, 2005 for PCT/US2004/007501.

D. Landolt, "Fundamental Aspects of Electropolishing", Mar. 18, 1996, pp. 1-11.

Partial International Search Report for US 02/40754 dated Apr. 28, 2003.

PCT International Preliminary Examination Report for PCT/US02/04806, dated Sep. 7, 2004.

PCT International Preliminary Examination Report for PCT/US03/06058, dated Sep. 7, 2004.

PCT International Search Report for US 03/06058 dated Jun. 25, 2003.

PCT Written Opinion for PCT/US02/04806, dated Mar. 9, 2004.

PCT Written Opinion for PCT/US03/06058, dated Feb. 13, 2004.

PCT Invitation to Pay Additional Fees for PCT/US04/006385 dated Mar. 22, 2005.

PCT International Search Report for PCT/US04/006385 dated May 17, 2005.

PCT Written Opinion for PCT/US04/006385 dated May 17, 2005.

PCT Invitation to Pay Additional Fees for PCT/US04/006385 dated Mar. 22, 2005.

PCT International Search Report for PCT/US04/006385 dated May 17, 2005.

PCT Written Opinion for PCT/US04/006385 dated May 17, 2005.

PCT International Search Report for US 02/04806 dated Apr. 1, 2003.

PCT International Search Report, EPO International Searching Authority, Mail Date Jan. 16, 2006, pp. 1-4.

NN436152, IBM Technical Disclosure Bulletin, "In-situ control and end point detection for plating cathodes", Aug. 2000, no author provided.

Alexander, et al., "Electrically Conductive Polymer Nanocomposite Materials", www.afrlhorizons.com/Briefs/Sept02/ML0206.html, date unknown.

Prosecution history of U.S. Appl. No. 11/949,160 as of May 20, 2010.
Prosecution history of U.S. Appl. No. 11/464,851 as of May 20, 2010.
Prosecution history of U.S. Appl. No. 11/391,324 as of May 20, 2010.
Prosecution history of U.S. Appl. No. 11/244,688 as of May 20, 2010.

\* cited by examiner

ENDPOINT FOR ELECTROPROCESSING

This application is a continuation of U.S. patent application Ser. No. 10/949,160, filed Sep. 24, 2004 now abandoned. Patent application Ser. No. 10/949,160 is a continuation-in-part of U.S. patent application Ser. No. 10/456,851, filed Jun. 6, 2003, now U.S. Pat. No. 7,112,270 entitled "ALGORITHM FOR REAL TIME PROCESS CONTROL OF ELECTRO-POLISHING", which is a continuation-in-part of U.S. patent application Ser. No. 10/244,688, filed Sep. 16, 2002, now U.S. Pat. No. 6,848,970 entitled PROCESS CONTROL IN ELECTROCHEMICALLY ASSISTED PLANARIZATION and U.S. patent application Ser. No. 10/391,324, filed Mar. 18, 2003, now abandoned entitled PROCESS CONTROL IN ELECTRO-CHEMICAL MECHANICAL POLISHING. Benefit of priority from all the above referenced applications is claimed. All the above-reference applications are also incorporated by reference herein in their entireties.

BACKGROUND OF THE INVENTION

1. Field of the Invention

The present invention generally relates to polishing, planarization, plating and combinations thereof. More particularly, the invention relates to the monitoring and control of electro-processing, polishing and plating.

2. Description of the Related Art

Sub-quarter micron multi-level metallization is one of the key technologies for the next generation of ultra large-scale integration (ULSI). The multilevel interconnects that lie at the heart of this technology require planarization of interconnect features formed in high aspect ratio apertures, including contacts, vias, trenches and other features. Reliable formation of these interconnect features is very important to the success of ULSI and to the continued effort to increase circuit density and quality on individual wafers and die.

In the fabrication of integrated circuits and other electronic devices, multiple layers of conducting, semiconducting, and dielectric materials are deposited on or removed from a surface of a wafer. Thin layers of conducting, semiconducting, and dielectric materials may be deposited by a number of deposition techniques. Common deposition techniques in modern processing include physical vapor deposition (PVD), also known as sputtering, chemical vapor deposition (CVD), plasma-enhanced chemical vapor deposition (PECVD), and electro-chemical plating (ECP).

As layers of materials are sequentially deposited and removed, the uppermost surface of the wafer may become non-planar across its surface and require planarization. An example of a non-planar process is the deposition of copper films with the ECP process in which the copper topography simply follows the already existing non-planar topography of the wafer surface, especially for lines wider than 10 microns. Planarizing a surface, or "polishing" a surface, is a process where material is removed from the surface of the wafer to form a generally even, planar surface. Planarization is useful in removing undesired surface topography and surface defects, such as rough surfaces, agglomerated materials, crystal lattice damage, scratches, and contaminated layers or materials. Planarization is also useful in forming features on a wafer by removing excess deposited material used to fill the features and to provide an even surface for subsequent levels of metallization and processing.

Chemical Mechanical Planarization, or Chemical Mechanical Polishing (CMP), is a common technique used to planarize wafers. CMP utilizes a chemical composition, typically a slurry or other fluid medium, for selective removal of materials from wafers. In conventional CMP techniques, a wafer carrier or polishing head is mounted on a carrier assembly and positioned in contact with a polishing pad in a CMP apparatus. The carrier assembly provides a controllable pressure to the wafer, thereby pressing the wafer against the polishing pad. The pad is moved relative to the wafer by an external driving force. The CMP apparatus effects polishing or rubbing movements between the surface of the wafer and the polishing pad while dispersing a polishing composition to affect chemical activities and/or mechanical activities and consequential removal of materials from the surface of the wafer.

Another planarization technique is Electro Chemical Mechanical Polishing (ECMP). ECMP techniques remove conductive materials from a wafer surface by electrochemical dissolution while concurrently polishing the wafer with reduced mechanical abrasion compared to conventional CMP processes. The electrochemical dissolution is performed by applying a bias between a cathode and a wafer surface to remove conductive materials from the wafer surface into a surrounding electrolyte. Typically, the bias is applied by a ring of conductive contacts to the wafer surface in a wafer support device, such as a wafer carrier head. Mechanical abrasion is performed by positioning the wafer in contact with conventional polishing pads and providing relative motion therebetween.

An objective of polishing is to remove a predictable amount of material to achieve a desired profile. Accordingly, any polishing technique requires an endpoint detection to determine when the appropriate amount of material has been removed for various regions of the wafer. However, the progress of the polishing operation is not easily viewable because of the contact between the wafer and the pad.

In addition, variations in the polishing conditions impede an accurate determination of the polishing endpoint. Variations in the slurry/electrolyte composition, pad condition, relative speed between the pad and the wafer, and the load of the wafer on the pad, etc, cause variations in the material removal rate, which change the time needed to reach the polishing endpoint. Therefore, the polishing endpoint cannot be estimated merely as a function of polishing time.

One approach to predict the polishing endpoint is to remove the wafer from the polishing apparatus and measure the thickness of the remaining film on the wafer. Doing so periodically during polishing, the quantity of material being removed from the wafer may be determined. As such, a linear approximation of the material removal rate may be used to determine the polishing endpoint. However, this method is time consuming, and does not account for sudden changes in the removal rate that may occur between measurement intervals.

Several non-invasive methods of endpoint detection are known. One type of endpoint detection typically requires access to at least a portion of the wafer surface being polished, such as by sliding a portion of the wafer over the edge of the polishing pad or through a window in the pad, and simultaneously analyzing the exposed portion of the wafer. For example, where polishing is used to expose metal lines embedded in a dielectric layer, the overall or composite reflectivity of the surface being polished changes as the lines are exposed. By monitoring the reflectivity of the polished surface or the wavelength of light reflected from the surface, the exposure of the lines through the dielectric layer, and thus the polishing endpoint, can be detected. However, this method does not provide a way of determining the polishing endpoint unless an underlying layer is exposed during polishing. Additionally, this approach is somewhat erratic in predicting the polishing endpoint unless all of the underlying lines are simultaneously exposed. Furthermore, the detection apparatus is delicate and subject to frequent breakdown caused by the exposure of the measuring or detecting apparatus to the slurry or electrolytic fluid.

A second type of method for determining the polishing endpoint monitors various process parameters, and indicates an endpoint when one or more of the parameters abruptly change. For example, the coefficient of friction at the interface of the polishing pad and the wafer is a function of the surface condition of the wafer. Where an underlying material different from the film being polished is exposed, the coefficient of friction will change also. This affects the torque necessary to provide the desired polishing pad speed. By monitoring this change, the endpoint may be detected.

In an ideal system, where no parameter other than the wafer surface changes, process parameter endpoint detection is acceptable. However, as the wafer is being polished, the pad condition and the slurry/electrolyte composition at the pad-wafer interface also change. Such changes may mask the exposure of the underlying metal layer, or they may imitate an endpoint condition, leading to a premature stop of polishing.

Finally, ECMP presents a chemically, electrically and physically unique environment, with respect to conventional CMP. Thus, while the endpoint detection techniques (including those described above) exist for CMP, the techniques may not be readily extendible to ECMP. Even where the techniques are extendible to ECMP, doing so may require retrofitting existing processing systems with expensive equipment. A preferred approach would mitigate or avoid the challenges with retrofitting existing systems.

Therefore, there is a need for polishing control, and in particular there is a need for endpoint detection, which accurately and reliably determines when to cease polishing during electro-processing.

SUMMARY OF THE INVENTION

In general, embodiments are relating to process control of electro-processing. Some aspects of the invention are generally directed to determining removal of material from a wafer during polishing, to determining an endpoint of a polishing cycle, and to adjusting the endpoint in-situ. Other aspects are directed to determining target charge (current integrated over time) values for a plurality of electrode zones (e.g., two or more) which can be independently biased.

In one embodiment, the method includes processing a conductive layer formed on a wafer using a target endpoint, detecting breakthrough of the conductive layer to expose portions of an underlying layer, and adjusting the target endpoint in response to the detected breakthrough. In another embodiment, the target endpoint is adjusted relative to an amount of underlying layer exposed through the conductive layer.

BRIEF DESCRIPTION OF THE DRAWINGS

So that the manner in which the above recited embodiments are attained and can be understood in detail, a more particular description may be had by reference to the appended drawings. It is to be noted, however, that the appended drawings illustrate only typical embodiments of this invention and are therefore not to be considered limiting of its scope, for the invention may admit to other equally effective embodiments.

To facilitate understanding, identical reference numerals have been used, where possible, to designate identical elements that are common to the Figures.

Figure 1:
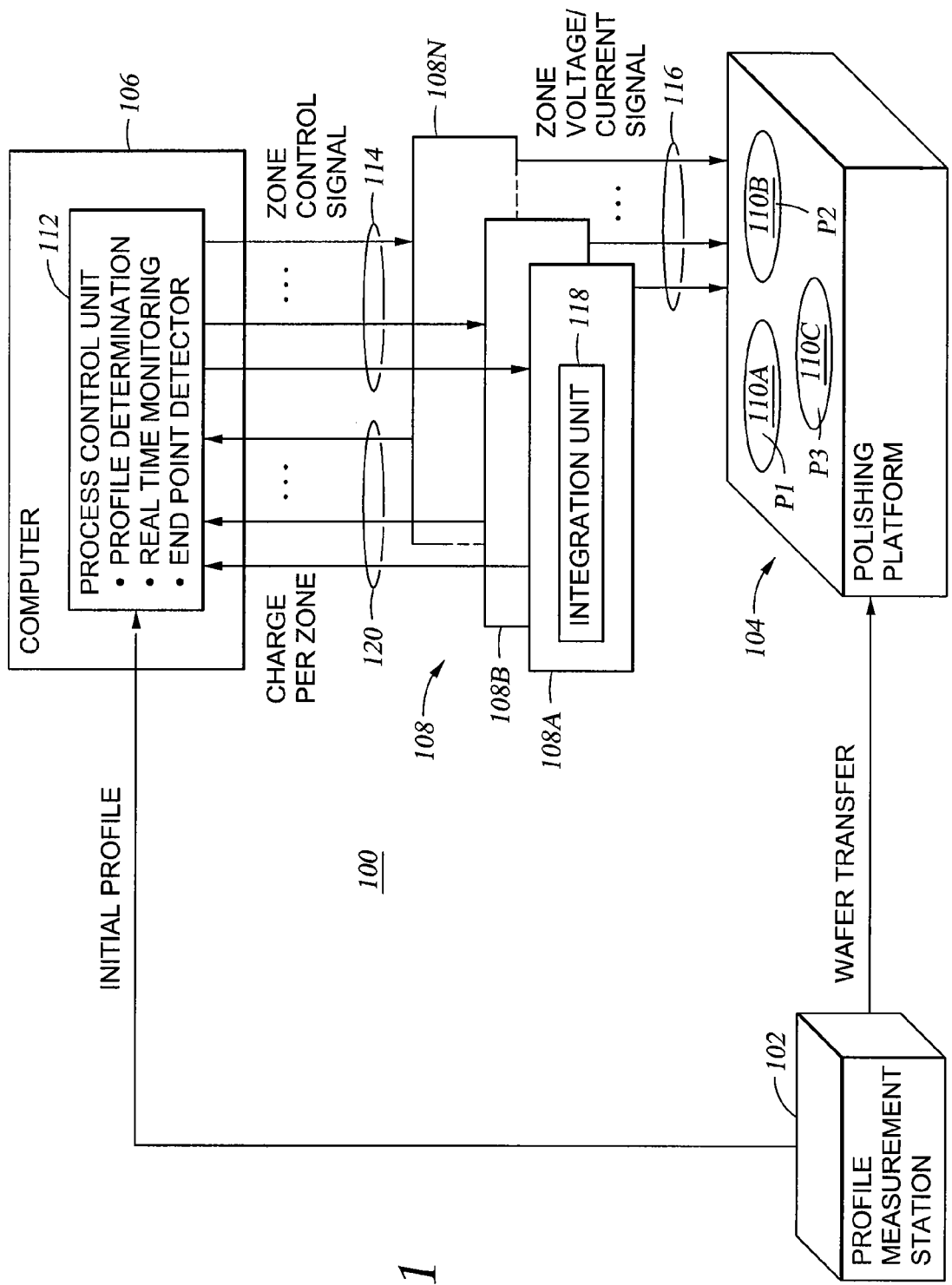
FIG. 1 is a perspective view of one embodiment of a processing environment having a profile measurement station, an electro-processing platform and a computer for controlling processes performed on the platform.

It is to be noted, however, that the appended drawings illustrate only exemplary embodiments of this invention and are therefore not to be considered limiting of its scope, for the invention may admit to other equally effective embodiments.

DETAILED DESCRIPTION

The present invention provides systems and methods for electro-processing wafers. Generally, electro-processing is performed to remove or deposit material on the wafer. Embodiments are provided for determining a profile for a wafer, calculating charge values and detecting an endpoint of an electro-processing cycle. In one embodiment, an electro-processing system is provided with a plurality of power supplies each connected to a different zone of an electrode. The power supplies are independently controlled to provide a desired voltage/current signal to a respective zone. The current is monitored and related to the total removal/deposition of material from a wafer to determine the endpoint of the process.

The words and phrases used herein should be given their ordinary and customary meaning in the art by one skilled in the art unless otherwise further defined. A wafer refers to a workpiece which is typically disc-shaped, but may be otherwise (e.g., rectangular or square). The wafer is typically a substrate having one or more layers formed thereon, at least one of which is conductive (typically the upper-most layer). The layer(s) of the wafer may or may not be patterned. Chemical-mechanical polishing should be broadly construed and includes, but is not limited to, abrading a wafer surface (e.g., an upper-most conductive layer) by chemical activities, mechanical activities, or a combination of both chemical and mechanical activities. Electro-processing refers to any process using electrical activity to remove or deposit material on a wafer. Particular examples of electro-processing for removing material from a wafer include electro-polishing, electrochemical mechanical polishing, and electrochemical mechanical plating process. Electro-polishing should be broadly construed and includes, but is not limited to, planarizing a wafer by the application of electrical and/or electrochemical activity and a particular example includes electrochemical mechanical polishing. Electrochemical mechanical polishing (ECMP) should be broadly construed and includes, but is not limited to, planarizing a wafer by the application of electrochemical activity, mechanical activity, or a combination of both electrochemical and mechanical activity to remove materials from a wafer surface. Electrochemical mechanical plating process (ECMPP) should be broadly construed and includes, but is not limited to, electrochemically depositing material on a wafer and concurrently planarizing the deposited material by the application of electrochemical activity, mechanical activity, or a combination of both electrochemical and mechanical activity.

Embodiments of the invention broadly provide for real-time removal monitoring and endpoint detection in a electro-processing system. In general, any of the above-defined techniques may be used, individually or in combination. Further, it is contemplated that polishing and plating may occur simultaneously or alternately. The foregoing embodiments are broadly, collectively characterized as electro-processing. While embodiments are described primarily with reference to a form of electro-polishing, it is understood that the invention is not so limited. Rather, embodiments include any form of the electro-processing. Thus, any reference to particular embodiments of electro-polishing are merely for purposes of illustration.

FIG. 1 depicts wafer processing environment 100. The processing environment 100 includes a profile measurement station 102, an electrochemical mechanical polishing (ECMP) platform 104, a computer 106 and a plurality of power supplies 108A, 108B, ... 108N (collectively referred to as the power supplies 108). The profile measurement station 102 is generally any device or devices conFigured to measure film thickness profiles of wafers. Exemplary non-contact devices which may be used include iScan and iMap, which scan and map the wafer, respectively. In the illustrative embodiment of FIG. 1, the profile measurement station 102 represents an ex-situ device; that is, film thickness profile measurement is performed at a location different from where polishing is performed. However, in situ profile measurement (e.g., on the polishing platform 104) is also contemplated. In either case, the profile measurement station 102 measures a profile of a wafer (referred to as the "initial profile") and provides this measurement to the computer 106.

The polishing platform 104 may be any apparatus adapted for polishing wafers by electro-processes. One polishing platform that may be adapted to benefit from the invention is a REFLEXTION LK ECMP™ available from Applied Materials, Inc. located in Santa Clara, Calif.

Illustratively, the polishing platform 104 includes a plurality of polishing stations 110A-C. By way of example three polishing stations (P1, P2, P3) are shown. More generally, the polishing platform 104 may include any number of polishing stations (i.e., one or more). The polishing platform 104 may also include other process stations, such as rinse stations.

The processes performed on wafers by the polishing platform 104 are generally controlled by the computer 106. The computer 106 may be representative of, or include, any programmable device conFigured to carry out embodiments of the invention. Thus, in one embodiment, the computer 106 is representative of a controller or a plurality of controllers conFigured with code which, when executed, performs polishing operations. In other embodiments, the computer 106 may be characterized as a client computer, a server computer, a portable computer, an embedded controller, a PC-based server, a minicomputer, a midrange computer, a mainframe computer, and other computers adapted to support the methods, apparatus, and article of manufacture of the invention.

To implement desired polishing processes the computer 106 is conFigured with a process control unit 112. In one embodiment, the process control unit 112 is implemented in software, but may also be implemented in hardware. In either case, the code of the process control unit 112 defines functions of the preferred embodiment and can be contained on a variety of signal-bearing media (or computer readable media). The code (or the instructions implemented by such code) includes, but is not limited to, (i) information permanently stored on non-writable storage media, (e.g., read-only memory devices within a computer such as CD-ROM disks readable by a CD-ROM drive); (ii) alterable information stored on writable storage media (e.g., floppy disks within a diskette drive or hard-disk drive); or (iii) information conveyed to a computer by a communications medium, such as through a computer or telephone network, including wireless communications. The latter embodiment specifically includes information downloaded from the Internet and other networks. Such signal-bearing media, when carrying computer-readable instructions that direct the functions of the present invention, represent embodiments of the present invention.

In various embodiments, the process control unit 112 is capable of profile determination, real-time process monitoring and endpoint detection. These functions may be performed on the basis of various input, including the initial profile received from the profile measurement station 102. The process control unit 112 then causes the computer 106 to issue control signals 114 to each of the power supplies 108. In response to the control signals 114, the power supplies 108 each issue a separate electrical signal, collectively referred to as the electrical signals 116. Each of the electrical signals 116 provides a current/voltage to a separate one of a plurality of electrodes (e.g., two or more) of a given one of the polishing stations 110A-C. The individual electrodes receiving the control signals 114 are also referred to herein as "zones" of a single electrode. Accordingly, in one embodiment, each electrode/zone has an associated one of the power supplies 108. It is noted, however, that while separate power supplies may be used, a single unit capable of producing multiple electrical signals of different voltage/current may also be used. Therefore, the term "power supplies" as used herein does not necessarily denote physically separate power supplies. Also, the number of power supplies and respective electrodes/zones may be varied.

In one embodiment, during processing of a given wafer on one of the polishing stations 110A-C, removal of material from the wafer is measured as charge. In one embodiment, charge is calculated by integrating current with respect to time. As such, each of the power supplies 108 may be conFigured with an integration unit 118 which integrates the current being provided by the respective power supply to an electrode/zone of the polishing station. The output 120 (i.e., the charge per electrode/zone) of the integration units 118 is provided to the process control unit 112. Although shown as part of the power supplies 108, the integration units 118 may alternatively be part of the process control unit 112, or be separate units altogether. Each of the foregoing aspects will be described in more detail below.

Figure 2A:
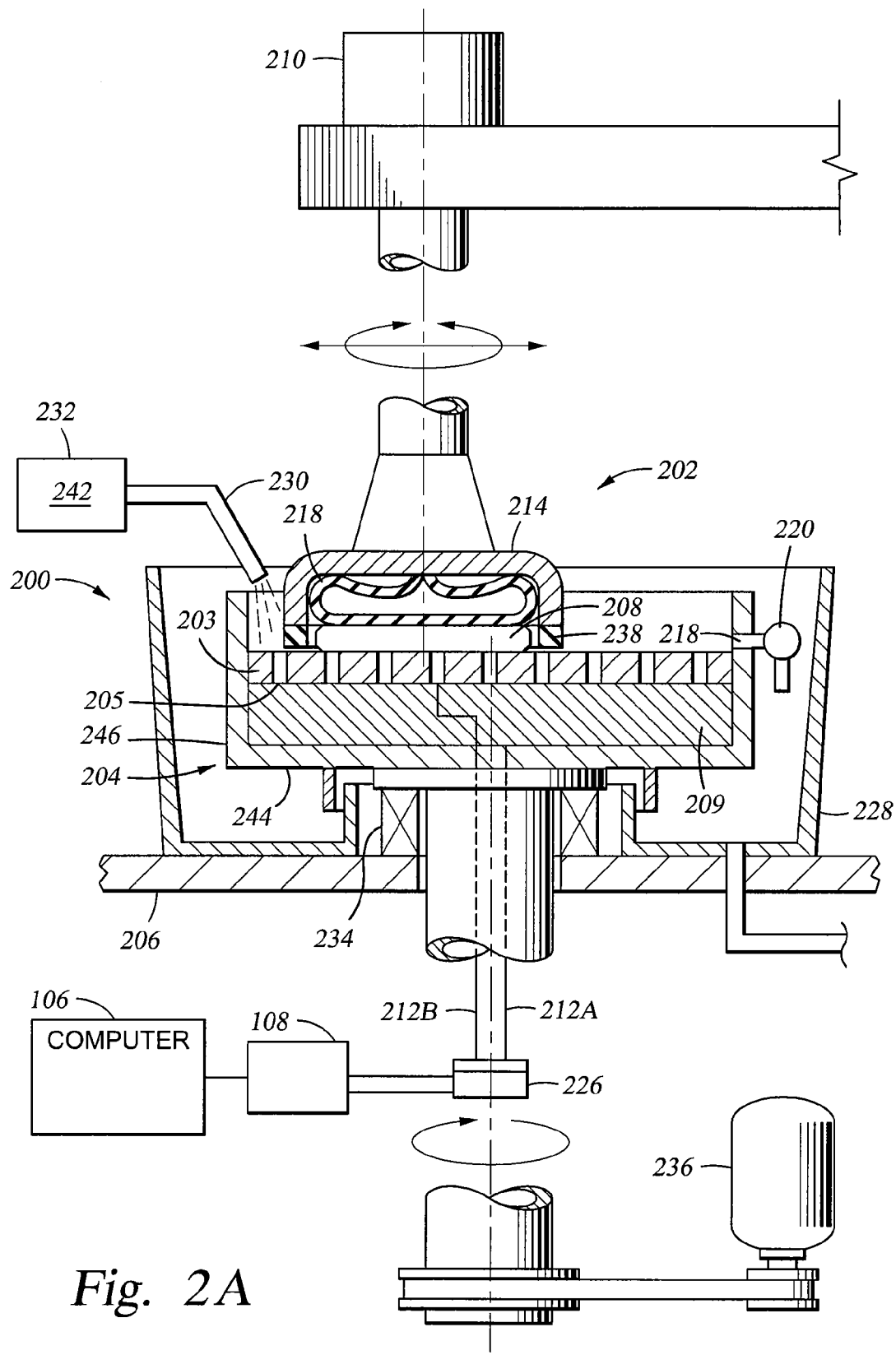
FIGS. 2A-B are side cross-sectional views of exemplary embodiments of an electro-polishing station.

Referring now to FIG. 2A, one embodiment of a process cell 200 is shown in side cross-section. The process cell 200 may be representative of a cell located at any one or all of the polishing stations 110A-C shown in FIG. 1. In particular, the polishing station 200 is a "face-down" polishing apparatus. However, embodiments using "face-up" polishing apparatus are also contemplated.

The process cell 200 generally includes a basin 204 and a polishing head 202. A substrate 208 is retained in the polishing head 202 and lowered into the basin 204 during processing in a face-down (e.g., backside up) orientation. An electrolyte is flowed into the basin 204 and in contact with the substrate's surface while the polishing head 202 places the substrate 208 in contact with a polishing article 203. In one embodiment, the substrate 208 and the polishing article 203 disposed in the basin 204 are moved relative to each other to provide a polishing motion (or motion that enhances plating uniformity). The polishing motion generally comprises at least one motion defined by an orbital, rotary, linear or curvilinear (e.g., sweep) motion, or combinations thereof, among other motions. The polishing motion may be achieved by moving either or both of the polishing head 202 and the basin 204. The polishing head 202 may be stationary or driven to provide at least a portion of the relative motion between the basin 204 and the substrate 208 held by the polishing head 202. In the embodiment depicted in FIG. 2A, the polishing head 202 is coupled to a drive system 210. The drive system 210 moves the polishing head 202 with orbital, rotary, linear, or curvilinear (e.g., sweep) motions, or combinations thereof.

The polishing head 202 generally retains the substrate 208 during processing. In one embodiment, the polishing head 202 includes a housing 214 enclosing a bladder 218. The bladder 218 may be deflated when contacting the substrate to create a vacuum therebetween, thus securing the substrate to the polishing head 202. The bladder 216 may additionally be inflated to press the substrate in contact with the polishing article 203. A retaining ring 238 is coupled to the housing 214 and circumscribes the substrate 208 to prevent the substrate from slipping out from the polishing head 202 while processing. One polishing head that may be adapted to benefit from the invention is a TITAN HEAD™ carrier head available from Applied Materials, Inc., located in Santa Clara, Calif.

The basin 204 is generally fabricated from a plastic such as fluoropolymers, TEFLON® polymers, perfluoroalkoxy resin, PFA, polyethylene-based plastics, PE, sulfonated polyphenylether sulfones, PES, or other materials that are compatible or non-reactive with electrolyte compositions that may be used in electroplating or electropolishing. The basin 204 includes a bottom 244 and sidewalls 246. The sidewalls 246 of the basin 204 include a port 218 formed therethrough to allow removal of electrolyte from the basin 204. The port 218 is coupled to a valve 220 to selectively drain or retain the electrolyte in the basin 204.

The basin 204 is rotationally supported above a base 206 by bearings 234. A drive system 236 is coupled to the basin 204 and rotates the basin 204 during processing. A catch basin 228 is disposed on the base 206 and circumscribes the basin 204 to collect processing fluids, such as an electrolyte, that flow out of port 218 disposed through the basin 204 during and/or after processing.

The basin 204 defines a housing for the polishing article 203 and an electrode assembly 209 which is disposed between the bottom 244 and the polishing article 203. In one embodiment, the polishing article 203 and the electrode 209 may be secured together forming a unitary body that facilitates removal and replacement. In one embodiment, the polishing article 203 and the electrode 209 are secured to one another by permanent means such as bonding. Alternatively, the polishing article 203 and the electrode 209 may be coupled by other techniques or combination thereof, including sewing, binding, heat staking, riveting, screwing and clamping among others. In still another embodiment the polishing article 203 is secured to a belt assembly which dispenses new (i.e., clean) pad material and takes up old (i.e., worn or contaminated) pad material.

As will be described in more detail with reference to FIG. 5, the electrode assembly 209 generally includes a plurality (e.g., at least two) of electrodes or zones. Each electrode is coupled to a lead 212A of one of the power supplies 108. The other lead 212B of each of the power supplies 108 is coupled to the polishing article 203, which is itself an electrode. For simplicity only one set of leads (positive and negative) is shown. Illustratively, the leads 212A-B are routed through a slip ring 226 disposed below the basin 204. The slip ring 226 facilitates continuous electrical connection between the power supplies 108 and the polishing article and electrode assembly 209 as the basin 204 rotates. The leads 212A-B may be wires, tapes or other conductors compatible with process fluids or having a covering or coating that protects the leads 212A-B from the process fluids. Examples of materials that may be utilized in the leads 212A-B include insulated copper, graphite, titanium, platinum, gold, and HASTELOY® materials among other materials. Coatings disposed around the leads 212A-B may include polymers such as fluorocarbons, PVC, polyamide, and the like.

In order to operate as an electrode, the polishing article 203 is made at least partially conductive by the provision of conductive material disposed in the polishing article 203. In general, the base material of the polishing article 203 may itself be made conductive, or conductive elements may be disposed in a non-conductive base material such as polyurethane. Particular embodiments of the polishing article 203 are described below.

In one embodiment, the electrode assembly 209 communicates electrically with the substrate 208 via perforations 205 formed in the polishing article 203. Thus, in one embodiment, the ability of the electrode assembly 209 to effect electro-processing is determined, in part, by the presence and location of the perforations 205. Specifically, it is contemplated that, in at least one embodiment, electro-processing is effected substantially only in those locations of the wafer 208 "visible" to the electrode assembly 209 through the perforations 205. Relatedly, it is contemplated that the proximity of the electrode assembly 209 to the wafer 208 affects processing. Generally, a closer proximity is preferred. Accordingly, in the illustrative embodiment of FIG. 2A, the electrode assembly 209 is shown directly interfacing with the polishing article 203. However, the provision of intermediate materials between the electrode assembly 209 and the polishing article 203 is also contemplated.

Figure 2B:
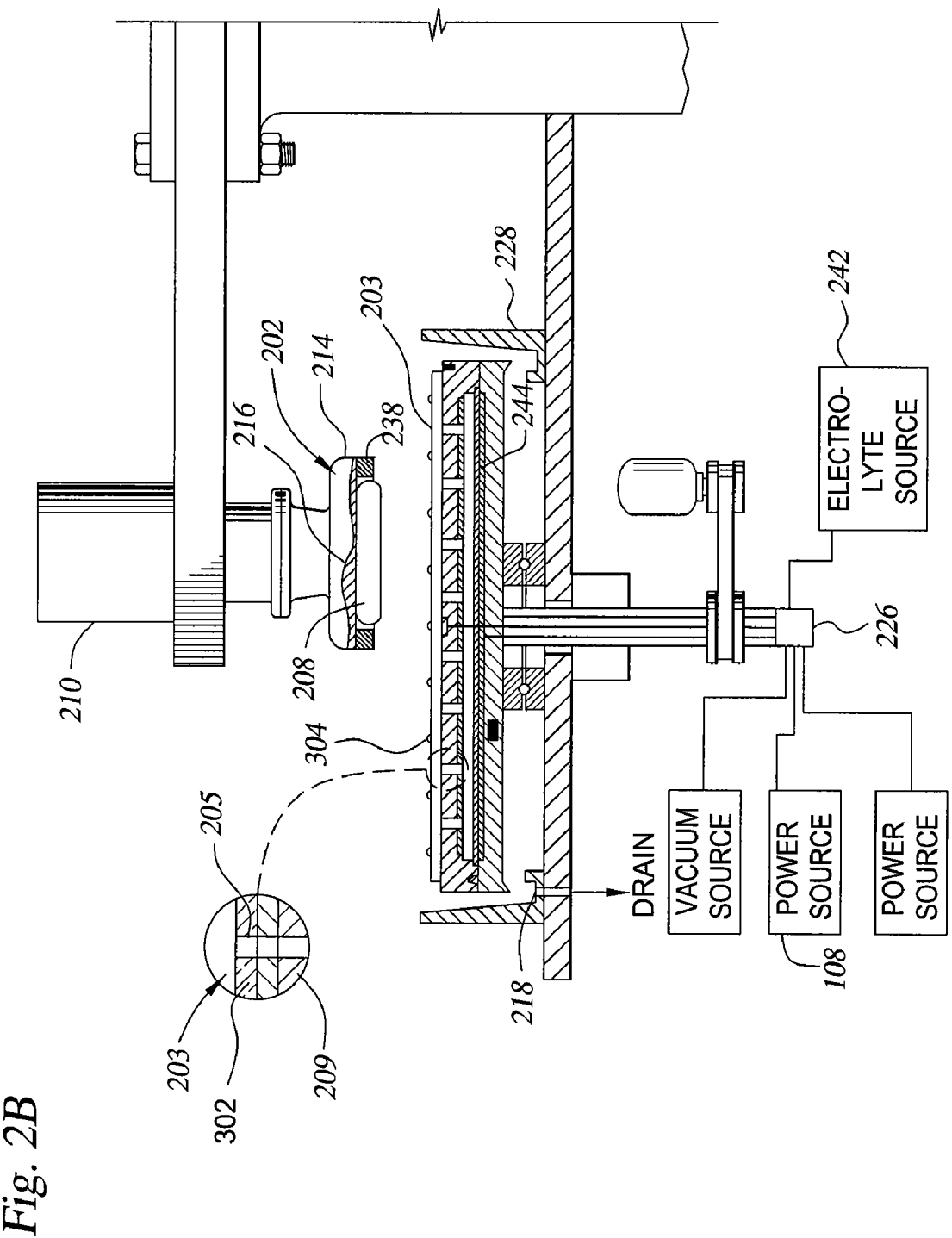

An electrolyte delivery system 232 is generally disposed adjacent the basin 204. The electrolyte delivery system 232 includes a nozzle or outlet 230 coupled to an electrolyte source 242. The outlet 230 flows electrolyte or other processing fluid from the electrolyte source 242 into the basin 204. During processing, the electrolyte generally provides an electrical path for biasing the substrate 208 and driving an electrochemical process to remove and/or deposit material on the substrate 208. Alternatively, the electrolyte delivery system may provide electrolyte through the bottom 244 of the process cell and flow electrolyte through the electrode assembly 209 and the perforations 205 of the polishing article 203 into contact with the substrate 208, as shown in the embodiment of FIG. 2B.

In operation, electrolyte is flowed into the basin 204 from the electrolyte delivery system 232. The electrolyte fills the basin 204 and is thus brought into contact with the wafer 208 and polishing article 203. To initiate electrochemical mechanical processing, potential differences are applied between the electrode assembly 209 and the conductive portion of the polishing article 203. The wafer 208 being in direct contact with the conductive portion of the polishing article 203 will then be at the same potential as the conductive portion. The current loop is then completed in the polishing station by transforming atomic wafer materials into ions in the electrolyte. Concurrent mechanical polishing of the wafer 208 is achieved by relative movement between the wafer and the polishing article 203. In one embodiment, polishing continues until reaching an endpoint, as determined by the process control unit 112. In at least one embodiment, "endpoint" refers to a point in time during a polishing cycle at which sufficient bulk metal has been removed from a wafer. Following detection of the endpoint, it may be necessary to continue polishing for a period of time in order to remove residual metal.

Figure 3:
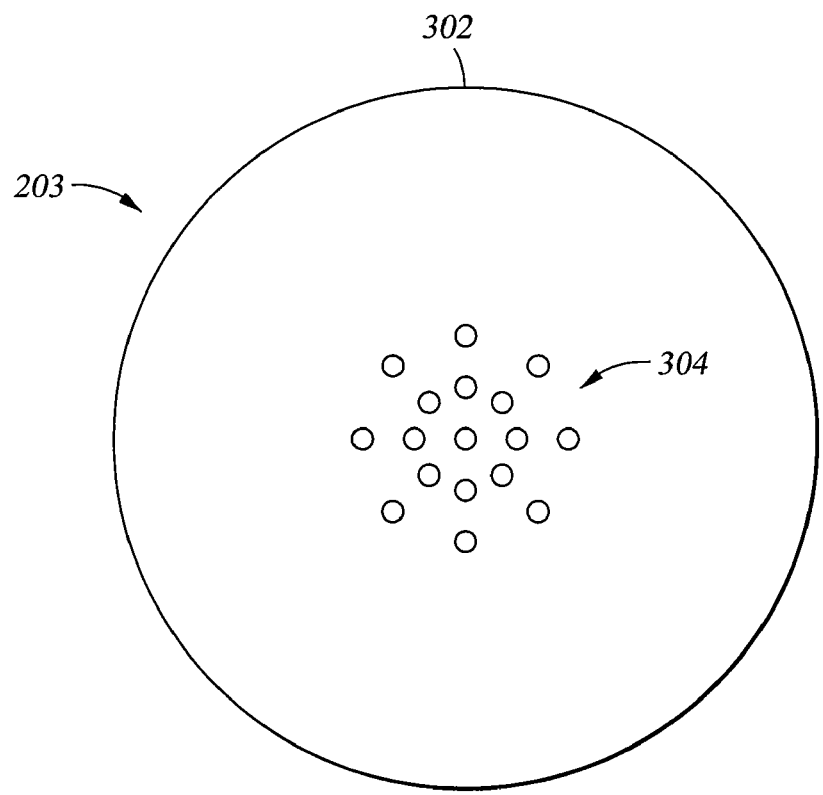
FIG. 3 is a top view of one embodiment of a polishing pad having contact elements disposed therein.

As noted above, the polishing article 203 is at least partially conductive. The conductivity of the polishing article may be accomplished in a variety of ways. Referring now to FIG. 3, one embodiment of the polishing article 203 is shown. In general, the polishing article 203 is a disk-shaped polishing pad 302 having a plurality of conductive elements 304 disposed thereon. For simplicity and clarity, the perforations 205 described above with reference to FIG. 2A are not shown. The polishing pad 302 may be made of polymeric materials, such as polyurethane, polycarbonate, polyphenylene sulfide (PPS), or combinations thereof, and other polishing materials used in polishing wafer surfaces. An exemplary conventional material includes those found in the IC series of polishing media, for example polyurethane and polyurethane mixed with fillers, commercially available from Rodel Inc., of Phoenix, Ariz. The invention further contemplates the use of other conventional polishing materials, such as a layer of compressible material. The compressible material may include a conventional soft material, such as compressed felt fibers leached with urethane. Further, the use of abrasive materials embedded in the polishing pad is contemplated. The fixed abrasive particles may include conductive abrasive materials and/or nonconductive abrasive materials.

The conductive elements 304 are shown disposed in a symmetrical pattern at a central region of the polishing pad 302. The pattern shown in FIG. 3 is merely illustrative and other patterns may be used. In addition, the number of conductive elements 304 may be varied. In one embodiment, the conductive elements 304 are rigidly fixed in place. In another embodiment, the conductive elements 304 are rotatably disposed relative to the polishing pad 302 so that the conductive elements 304 may rotate over the surface of a wafer brought into contact with the conductive elements 304. A variety of embodiments are described in U.S. patent application Ser. No. 10/210,972, filed Aug. 2, 2002, entitled CONTACTS FOR ELECTROCHEMICAL PROCESSING, herein incorporated by reference in its entirety.

Alternatively or additionally, the polishing article 203 is made conductive by making the polishing material itself of conductive material. The conductive polishing material may include conductive polymers, polymer composites with conductive materials, conductive metals, conductive fillers or conductive doping materials, or combinations thereof. Conductive polymers include polymeric materials that are intrinsically conductive, such as polyacetylene, polyethylenedioxythiophene (PEDT), polyaniline, polypyrrole, and combinations thereof. The polymer composites with conductive materials may include polymer-noble metal hybrid materials. Polymer-noble metal hybrid materials that may be used as the conductive polishing material described herein are preferably chemically inert with a surrounding electrolyte, such as those with noble metals that are resistant to oxidation. An example of a polymer-noble metal hybrid material is a platinum-polymer hybrid material. The invention also contemplates the use of polymer-noble metal hybrid materials, which are chemically reactive with a surrounding electrolyte, when the polymer-noble metal hybrid material is insulated from a surrounding electrolyte by another material. Conductive metals that may be used as the polishing material are those metals that are preferably relatively inert to chemical reactions with the surrounding electrolyte. Platinum is an example of a conductive metal that may be used as the polishing material. The conductive metals may form a portion or the entire polishing surface of the polishing material. When forming a portion of the polishing surface, the conductive metals are typically disposed in a conventional polishing material.

The conductive polishing materials may further include conductive fillers or conductive doping materials disposed in a binder material, such as the conductive polymers described above or a conventional polishing material. Examples of conductive fillers include carbon powder, carbon fibers, carbon nanotubes, carbon nanofoam, carbon aerogels, and combinations thereof. Carbon nanotubes are conductive hollow filaments of carbon material having a diameter in the nanometer size range. The conductive fillers or conductive doping materials are disposed in the binding material in an amount sufficient to provide a polishing medium having a desired conductivity. The binder material is typically a conventional polishing material.

Alternatively or additionally, the polishing article 203 may comprise a metal mesh disposed in the polishing material. The metal mesh may comprise a chemically inert conductive material, such as platinum. The metal mesh may also include materials, such as copper, that have been observed to react with the surrounding electrolyte if the metal mesh is chemically insulated from the electrolyte such as by a conformal layer of conventional material.

Other embodiments of conductive polishing pads which may be used to advantage are further described in U.S. patent application Ser. No. 10/033,732, filed Dec. 27, 2001, entitled CONDUCTIVE POLISHING ARTICLE FOR ELECTROCHEMICAL MECHANICAL POLISHING, Ser. No. 10/140,010, filed May 7, 2002, entitled CONDUCTIVE POLISHING ARTICLE FOR ELECTROCHEMICAL MECHANICAL POLISHING, Ser. No. 10/455,941 filed Jun. 6, 2003, entitled CONDUCTIVE POLISHING ARTICLE FOR ELECTROCHEMICAL MECHANICAL POLISHING, Ser. No. 10/455,895, filed Jun. 6, 2003, entitled CONDUCTIVE POLISHING ARTICLE FOR ELECTROCHEMICAL MECHANICAL POLISHING, Ser. No. 10/642,128, filed Aug. 15, 2003, entitled CONDUCTIVE POLISHING ARTICLE FOR ELECTROCHEMICAL MECHANICAL POLISHING and Ser. No. 60/516,680, filed Nov. 3, 2003, entitled COMPOSITE POLISHING PAD ASSEMBLY FOR ELECTROCHEMICAL MECHANICAL POLISHING (ECMP), each of which is hereby incorporated by reference in their entireties.

In any case, where the polishing article 203 is at least partially conductive, the polishing article 203 acts as an electrode in combination with a wafer during electro-processes. The electrode assembly 209 provides a plurality of counter-electrodes to the polishing article 203. One embodiment of the electrode assembly 209 is shown in FIG. 4, now described.

Figure 4:
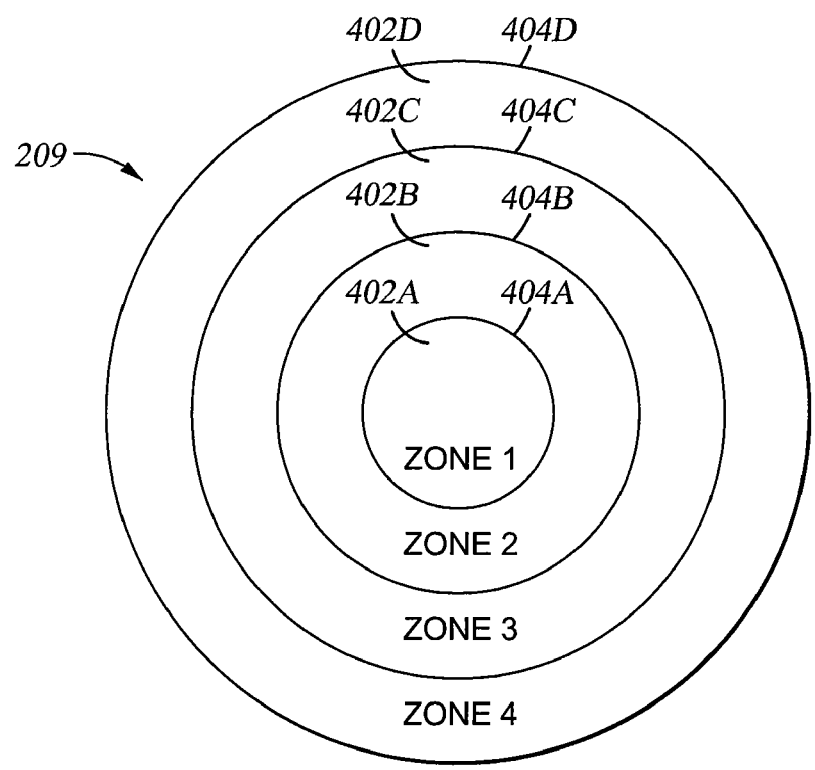
FIG. 4 is top view of one embodiment of an electrode assembly defining a plurality of zones.

FIG. 4 shows a top view of the electrode assembly 209. The electrode assembly 209 generally includes a plurality of electrodes. Specifically, four electrodes 402A-D (collectively, electrodes 402) are shown, although the electrode assembly 209 may include any number of electrodes. Illustratively, the electrodes 402 are annular members. In particular, an innermost electrode 402A is a disk, while the other electrodes 402B-D are rings. However, the electrodes may more generally be any geometry. Further, the electrodes 402 are conductive members made of, for example, a metal. For electrochemical removal processes, such as anodic dissolution, the electrodes 402 may include a non-consumable material other than the deposited material, such as platinum for copper dissolution. However, the electrodes 402 can also be made of copper for copper polishing, if preferred. Anodic dissolution should be broadly construed and includes, but is not limited to, the application of an anodic bias to a wafer directly or indirectly which results in the removal of conductive material from a wafer surface and into a surrounding electrolyte solution.

It is noted that for simplicity some features of embodiments of the electrode assembly 209 are not shown. For example, in one embodiment, the contact elements 304 are disposed through the innermost electrode 402A. The openings to receive the contact elements 304 are not shown in FIG. 4. The electrodes are separated from one another by annular gaps 404A-D (collectively, gaps 404). In one embodiment, insulating material may be disposed in the annular gaps 404. In illustrative configuration, each electrode 402 defines a zone, which can be separately biased by respective power supplies 108. Additional aspects in this regard may be described with reference to FIG. 5.

Figure 5:
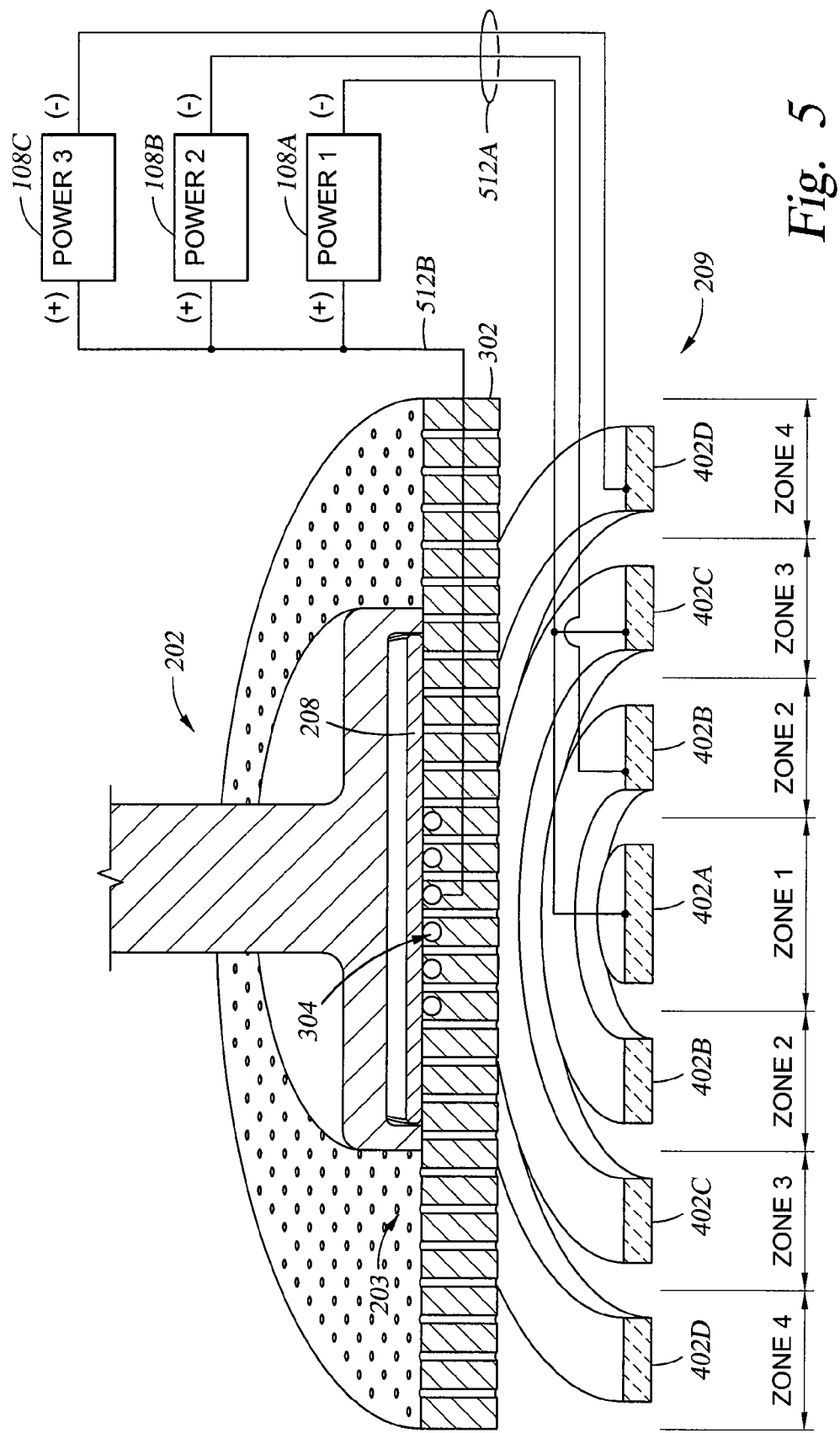
FIG. 5 is a side cross-sectional, exploded view of a polishing assembly which includes the polishing pad of FIG. 3 and the electrode assembly of FIG. 4.

FIG. 5 shows a side cross-sectional exploded view of the electrode assembly 209 and the polishing article 203. For purposes of illustration the polishing head 202 is also shown carrying a wafer positioned in contact with the upper polishing surface of the polishing pad 302. To facilitate illustration, the individual electrodes 402 of the electrode assembly 209 are shown exploded relative to the polishing pad 302 and relative to one another (i.e., the size of the gaps 404 between electrodes 402 have been exaggerated). FIG. 5 shows a representative configuration of three power supplies 108A-C with respect to the electrodes 402. In general, the individual electrodes 402 of the electrode assembly 209 may be anodes or cathodes depending upon the positive bias (anode) or negative bias (cathode) applied between the electrodes 402 and the polishing article 203. For example, depositing material from an electrolyte on the wafer surface, the electrodes 402 act as anodes and the wafer surface and/or polishing article 203 acts as a cathode. When removing material from the wafer 208, such as by dissolution from an applied bias, the electrodes 402 function as a cathode and the wafer surface and/or polishing article 203 may act as an anode for the dissolution process. In the illustrated embodiment, the electrodes 402 are connected to the negative leads 512A of the power supplies 108A-C, while the positive leads 512B are connected to the contact elements 304. (While the positive lead 512B is shown connected to only one of the contact elements 304 for simplicity, is understood that each of the contact elements 304 may be commonly connected to the positive lead 512B.) The embodiment of FIG. 5 illustrates that two or more electrodes 402 may be connected to the same power supply, and therefore be maintained at the same bias during processing. In the present illustration, the innermost electrode 402A and the outer, middle electrode 402C are connected to the same power supply 108A, while the inner, middle electrode 402B and the outer electrode 402D are connected to their own respective power supplies 108B and 108C, respectively. In this respect, the four member electrode assembly 209 may be considered a three zone assembly.

Figure 6:
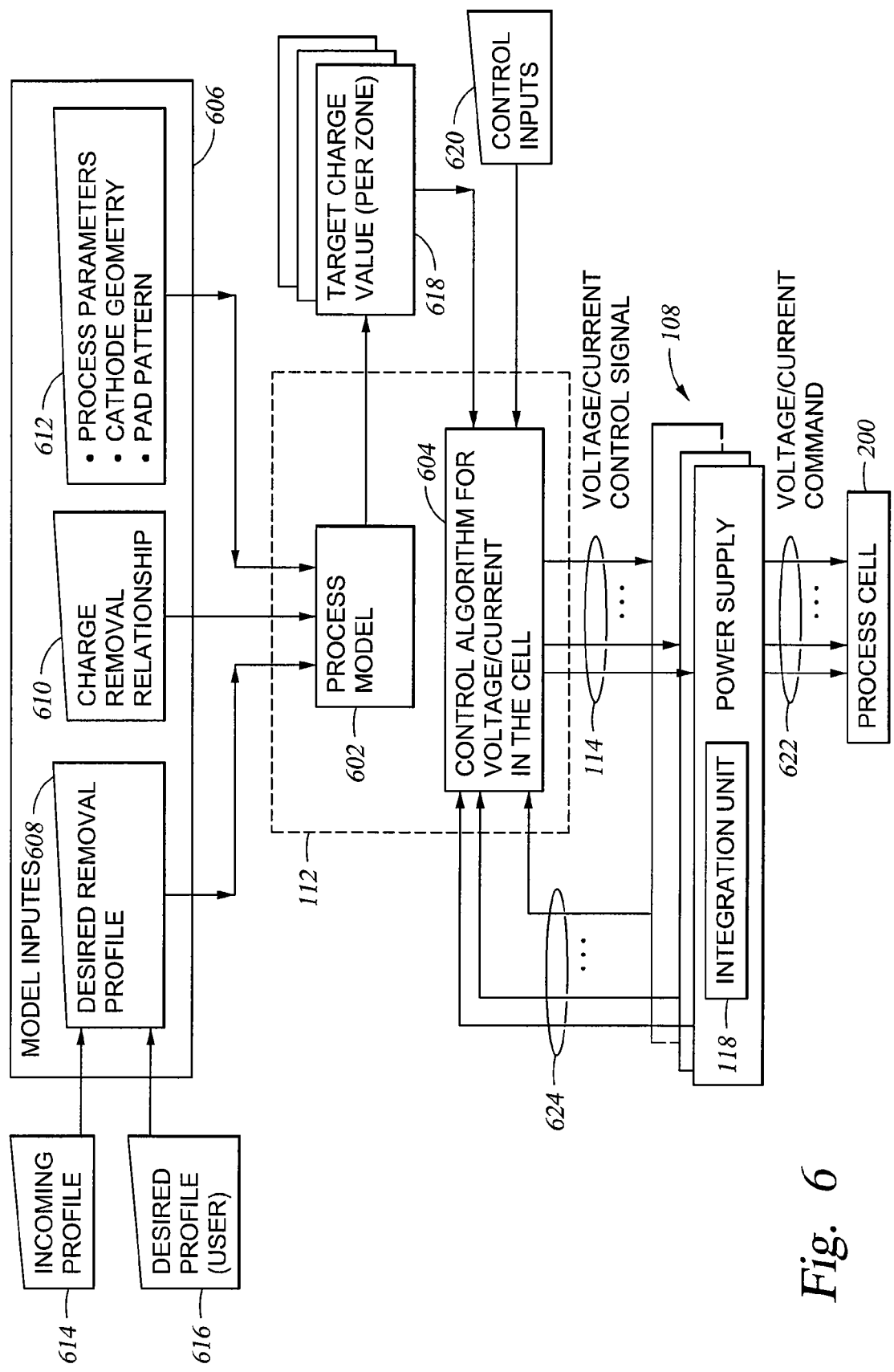
FIG. 6 is a block diagram of a process control unit conFigured for process monitoring and endpoint detection based on charge removed by various zones of the electrode assembly of FIG. 4.
Figure 7:
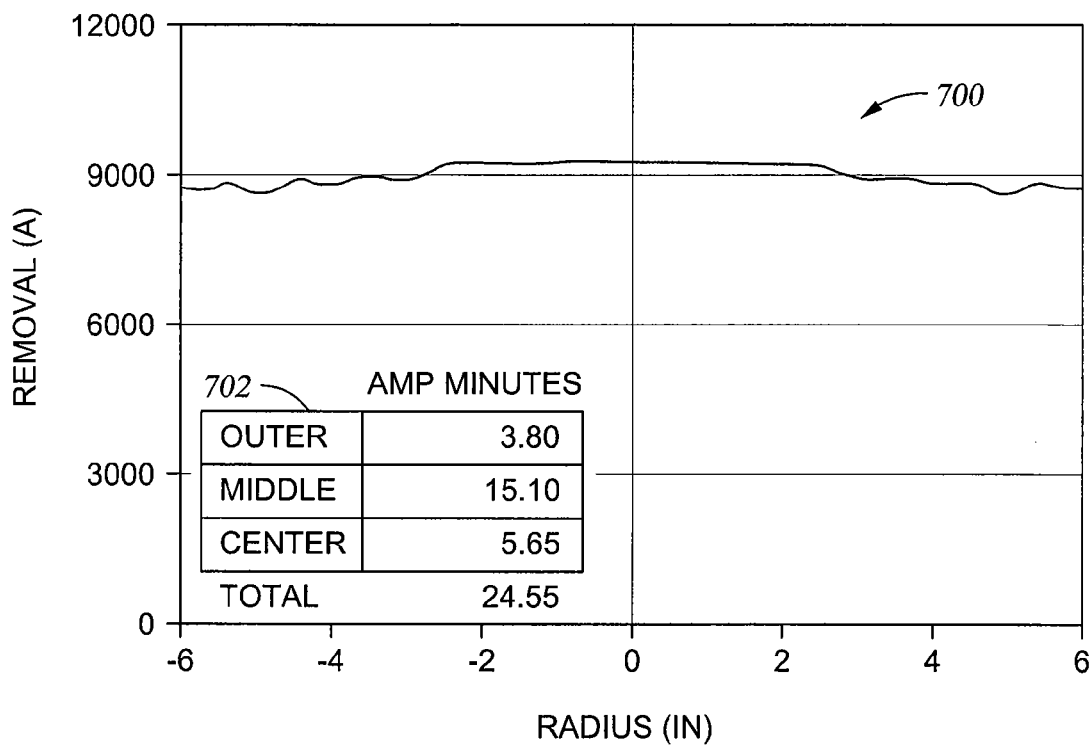
FIGS. 7-10 are graphs illustrating removal profiles for various charge values.
Figure 8:
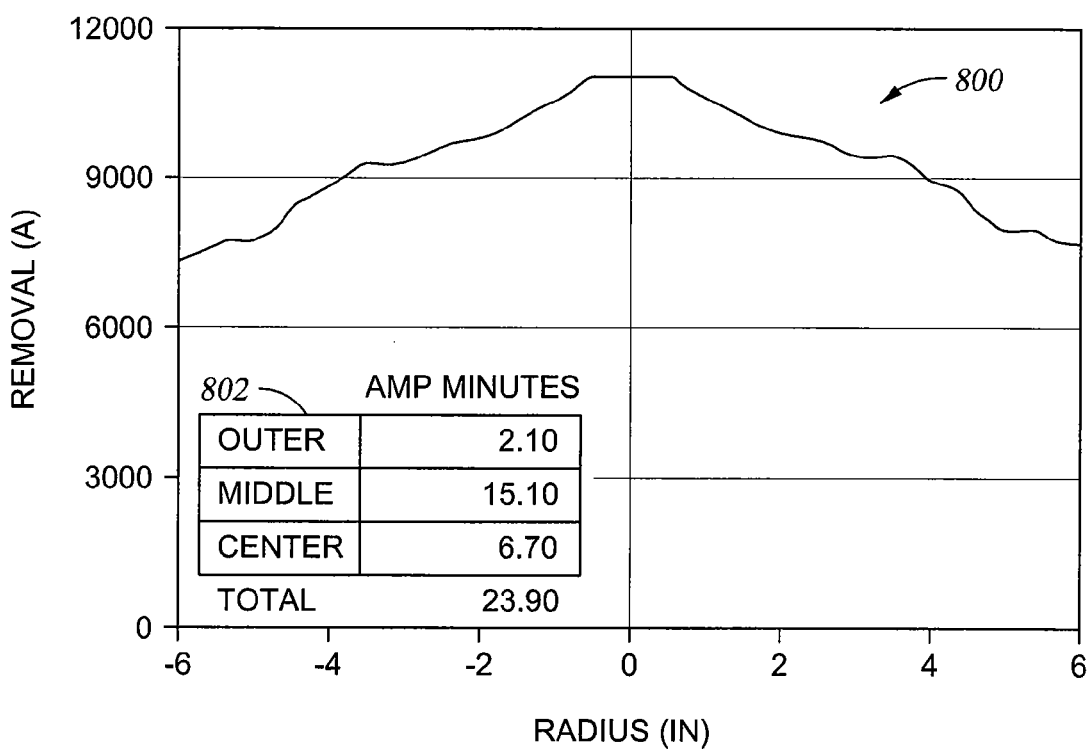
Figure 9:
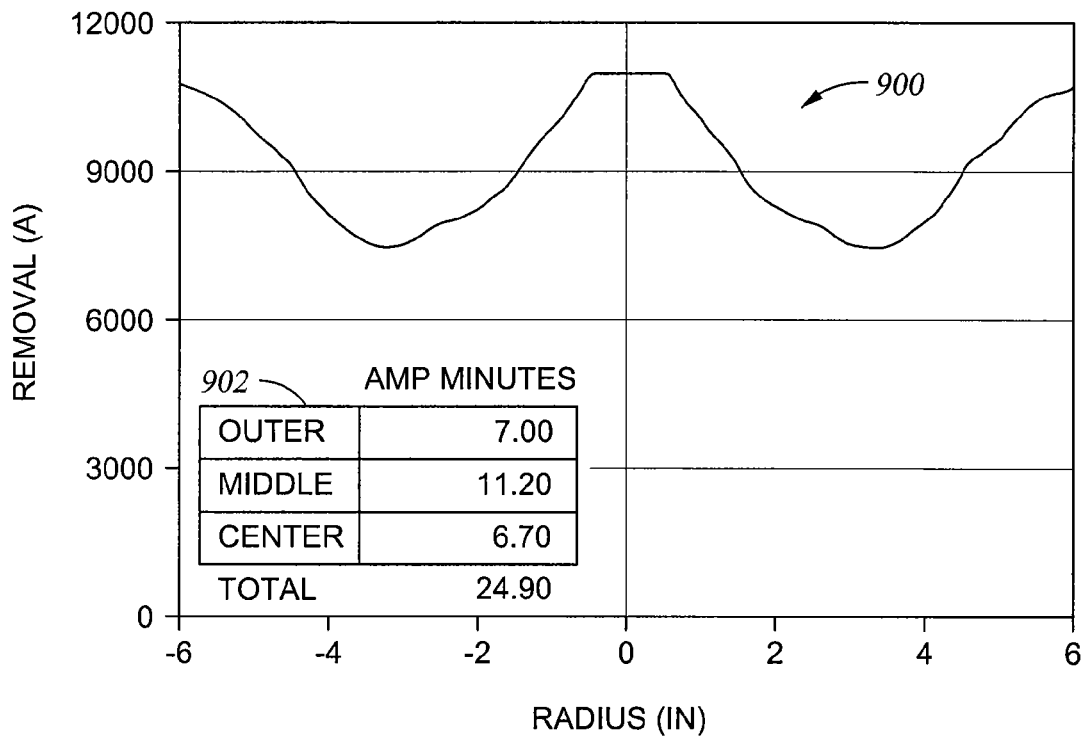
Figure 10:
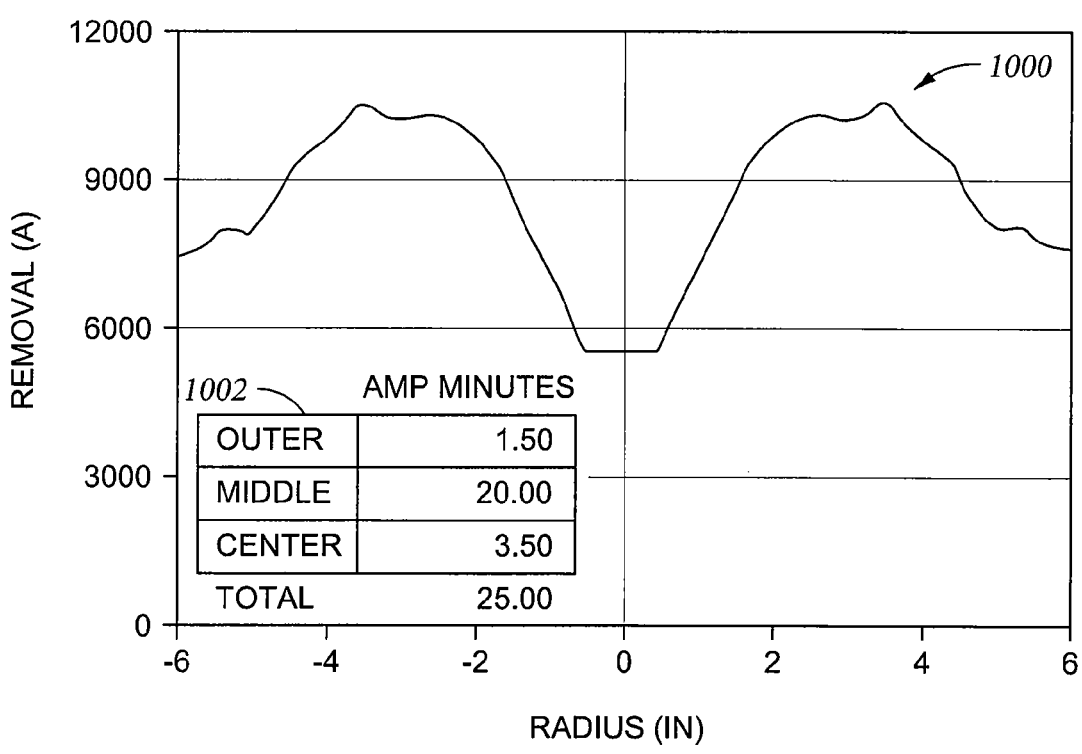

Referring now to FIG. 6, one embodiment of the process control unit 112 is shown. Generally, the process control unit 112 includes a process model 602 and a control algorithm 604. In general, the process model 602 describes a process environment. In operation, the process model 602 receives various model inputs 606. Based on the various model inputs 606, the process model 602 generates a target charge value for each zone defined by the electrode assembly 209 (the target charge values are collectively shown in FIG. 6 as the target charge values 618). In one embodiment, the model inputs 606 include a desired removal profile 608, a charge-removal relationship 610 and operations/cell parameters 612. The desired removal profile 608 describes a profile of the material to be removed from a wafer. In one embodiment, the desired removal profile is the simple arithmetic difference between a measured profile 614 (e.g., measured by the profile measurement station 102 shown in FIG. 1) and a desired profile 616, which may be user selected. The charge-removal relationship 610 describes a relationship between the amount of charge removed from a wafer and the thickness of material removed. The charge-removal relationship 610 is particular to a process and wafer type. Thus, a plurality of such relationships may be stored in a storage device and retrieved as needed. The operations/cell parameters 612 describe various aspects of the manner in which a wafer is processed and the cell in which the wafer is being processed and which may have an impact on the resulting removal profile of the wafer. Illustrative operations/cell parameters 612 include process parameters, electrode geometry, and polishing article construction. Process parameters may include, for example, platen rotation speed (i.e., rotation of the basin 204 in FIG. 2), head rotation speed (i.e., rotation speed of the polishing head 202 in FIG. 2), and sweep range and frequency. "Sweep" refers to the translation motion of the head along a radius of the platen (i.e., the bottom of the basin 204. With reference to construction of the electrode assembly 209 of FIG. 4, for example, electrode geometry refers to the geometry of the various electrodes 402 which make up the electrode assembly 209. Parameters pertaining to the polishing article construction include, for example, the geometry of the polishing pad (such as the polishing pad 302 shown in FIG. 3) and the placement of the contact elements (such as the contact elements 304 shown in FIG. 3). Additional aspects of the process model 602 and its inputs will be described in more detail below.

The target charge values 618 calculated by the process model 602 are provided as input to the control algorithm 604. In one embodiment, the control algorithm 604 receives additional control inputs 620, which may be operator selected. Illustrative control inputs include the total process time, the number of process steps and the like. The control algorithm 604 then generates a control signal (collectively, control signals 114) for each zone defined by the electrode assembly 209. The control signals 114 are provided to the respective ones of the power supplies 108. The control signals 114 may be conFigured to, for example, control current or voltage for the respective zone. Accordingly, the power supplies 108 produce corresponding electrical signals 622 for the respective zones. In addition, the charge removed per zone is calculated by each integration unit 118 of the power supplies 108.

The calculated charge per zone values 624 are fed back to the control algorithm 604. The control algorithm 604 then compares the calculated charge per zone values 624 to the respective target charge values 618. That is, the control algorithm 604 compares a calculated charge value for a particular zone to the corresponding target charge value for that zone. When the calculated charge value exceeds the corresponding target charge value, the bias for that zone is terminated. When each of the biases has been terminated, the electro-process is complete. Thus, in one aspect, the process control unit 112 provides for endpoint detection. In another aspect, the calculated charge values for each zone can be used to generate and display the profile of a wafer in real time.

It is noted that the control algorithm 604 can implement the control signals 114 according to any variety of functions depending, at least in part, on the control inputs 620. In one embodiment, the voltage in each zone is fixed. The voltage in each zone is then independently terminated once the target charge is achieved. The voltage in each zone may be selected according to parameters which include removal rate, planarization capability, surface roughness, defect count, etc. In another embodiment, the polishing time is fixed. In this case, the voltage for each zone is modulated (i.e. changed with respect to time) so that the target charge is met for each zone when the predefined polishing time expires. While the former embodiment provides simplicity, the latter embodiment allows better control of the step time. In some embodiments, a zone voltage may be zero or negative, while other contemporaneous zone voltages are positive. It is also contemplated that the voltages may be applied prior to any mechanical polishing, during mechanical polishing and/or after mechanical polishing. Persons skilled in the art will recognize other embodiments.

By way of example only, FIGS. 7-10 show illustrative incoming profiles 700, 800, 900, and 1000, respectively. The profiles are plotted on an x-y graph, where the x-axis is the wafer radius in inches and the y-axis is thickness in angstroms. The removal profiles should match these profiles in order to achieve the desired target profile. The charge values for each of the removal profiles are given in corresponding tables 702, 802, 902 and 1002. In particular, charge values are given for an outer zone, a middle zone and a center zone. The cathode geometry used was substantially similar to that shown in FIG. 4, in which zone 1 (defined by the innermost electrode 402A) and zone 3 (defined by the outer middle electrode 402C) were held at the same voltage. Accordingly, zone 1 and zone 3 are collectively referred to in FIGS. 7-10 as the "middle" zone. The "outer" zone corresponds to zone 4 and the "center" zone corresponds to zone 2 of the electrode assembly 209 shown in FIG. 4.

Charge-Removal Relationship

Figure 11:
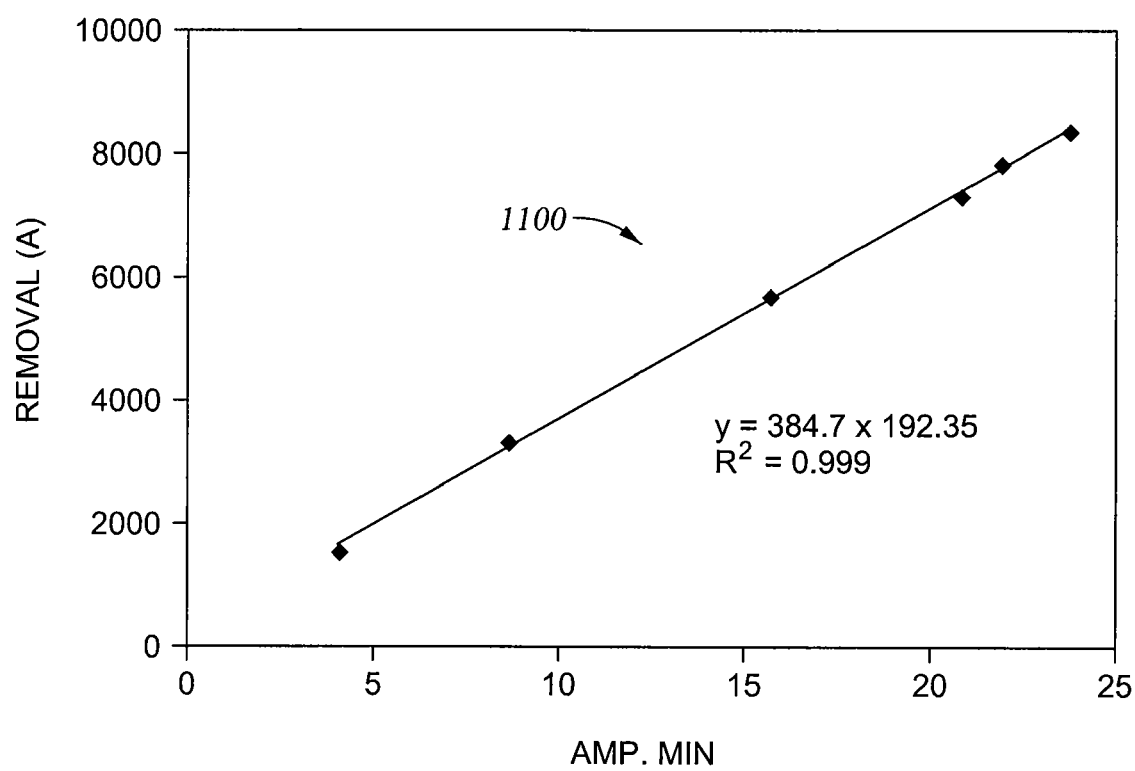
FIG. 11 shows one example of an empirically determined curve relating total charge and material removed.

As noted above, the process model 602 receives as an input a charge-removal relationship. In one embodiment, the charge-removal relationship is determined empirically, by periodically measuring (e.g., by sheet resistance measurements) the amount of material removed from a wafer being polished. Alternatively, the current may be measured for a series of wafers processed at different conditions (e.g., slightly different polishing times, voltage biases, etc.). In this manner, a calibration curve can be acquired. One such calibration curve 1100 is shown in FIG. 11. In this case, 9 wafers (1 per data point and 3 per zone in a three-zone electrode arrangement) were polished under different conditions and the average current was recorded. The thicknesses of the wafers were measured before and after the polishing cycle to determine the average amount of material removed. The calibration curve (expressed as y=348.7x+192.35) exhibits a linear relationship between the Removal (given in angstroms and shown on the y-axis) and the Charge (given in amperes*minutes and shown on the x-axis) and allows for the prediction (by extrapolation) of removal for a given current. Additional embodiments for determining such a relationship are described in U.S. patent application Ser. No. 10/391,324, filed Mar. 18, 2003, entitled PROCESS CONTROL IN ELECTRO-CHEMICAL MECHANICAL POLISHING, which is hereby incorporated by reference in its entirety, to the extent not inconsistent with the present embodiments.

In a particular embodiment, a charge-removal relationship may be determined by polishing a plurality of test material layers using a process cell such as the process cells of FIGS. 2A-B. The test material layers may be polished according to a specific set of instructions that may include a relative motion between a polishing pad and a wafer. The relative motion may be, for example, linear, curvilinear, rotational, orbital, or combinations thereof. A test bias, $V_t$ is then applied between the test material layer and the counter electrodes of the electrode assembly 209. The test bias, $V_t$, may be applied such that a substantially uniform potential is generated across the counter electrodes with respect to the surface to be polished. The bias may be applied to the test material layer using, for example, a pad such as the pad 302 described above in FIG. 3.

Figure 12:
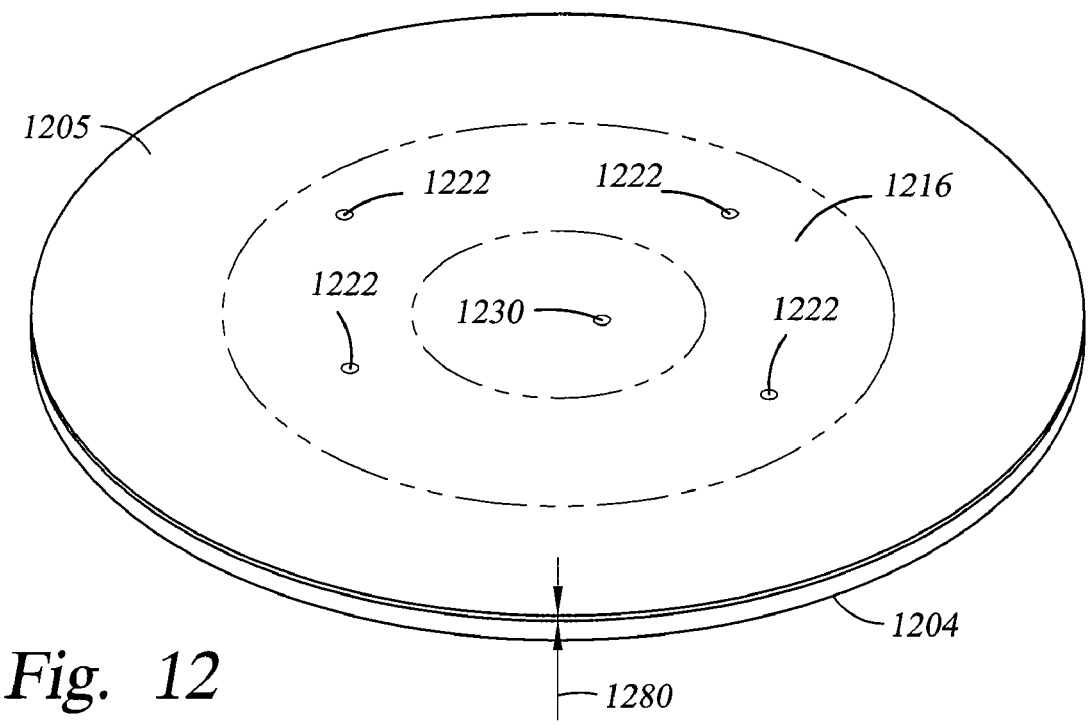
FIG. 12-13 are top perspective views of a substrate having a material layer thereon, wherein the material layer may be polished in order to develop a relationship between removal and charge.
Figure 13:
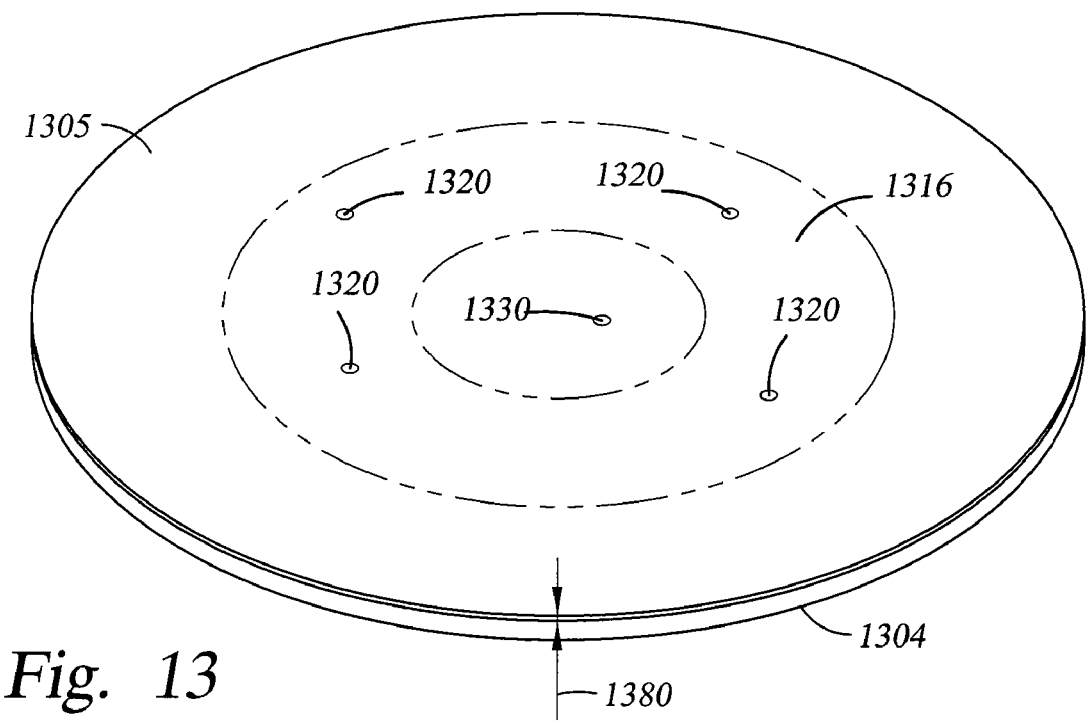

Referring now to FIG. 12, a top perspective view of a substrate 1204 shows a first test material layer 1205 formed thereon. Similarly, FIG. 13 shows a second substrate 1304 having a second test material layer 1305 formed thereon. The first test material layer 1205 is polished by applying a first test bias such as a uniform test bias across the test material layer 1205 relative to the counter electrodes of the electrode assembly 209.

After polishing the test material layer 1205 for a pre-determined period of time (a first polishing time), the substrate 1204 is, for example, removed from the process cell 100 and an amount of material removed from the test material layer 1205 is then measured. The amount of material removed may be determined, for example, using conventional methods of measuring layer thicknesses, such as sheet resistance (Rs) measurements. Alternatively, the amount of material removed may be measured using electron microscopy, or similar methods for analyzing thickness and composition of material layers. The material removal may be determined by measuring a thickness 1280 of the test material layer 1205 before polishing and the thickness 1280 after polishing. The thickness 1280 may be measured at a first point 1220. Additional thickness measurements of the first test material layer 1205 may be taken at one or more additional points 1222 in order to obtain a statistically representative value for material removal. Alternatively, a property other than thickness may be measured. For example, a mass of material removed or a material removal rate may be measured directly or indirectly. The one or more additional points 1222 on the test material layer 1205 may be chosen such that the points lie within a region or zone of the test material layer 1205 that experiences a relatively uniform rate of polishing (material removal). For example, the first point 1222 and the additional points 1222 may be chosen such that they all lie in an intermediate region 1216 of the test material layer 1205. Alternatively, the first point 1222 and the additional points 1222 may be chosen such that they each are a distance from a center 1230 of the test material layer 1205 that is substantially the same. A first rate of material removal may be determined by, for example, dividing mass or thickness of the material removed by the first polishing time.

The second test material layer 1305 may be polished using the same geometry and configuration of the process cell as for the polishing of the first test material layer 1205. The second test material layer 1305 may be polished to a thickness 1380 by applying a second bias applied to the second test material layer 1305. Thereafter, the step of determining material removal may be performed for one or more points 1320 on the second test material layer 1305. Furthermore, the process of determining removal rate may be repeated for additional test material layers (not shown), if desired.

The one or more points 1320 on the test material layer 1305 may lie, for example, within an intermediate region 1316. The intermediate region 1316 may have a similar shape and define a similar range of distances from a center 1330 of the material layer 1305 as is defined by the intermediate region 1216 with respect to the center 1230.

By matching the material removal from each test material layer 1205, 1305 with the corresponding charge (current integrated over time) removed from the test material layer, a relationship between material removed and charge may be determined. The relationship thus determined may be relevant for a specific configuration of the process cell, including a specific polishing composition as well as specific composition of material layer. The relationship may be a linear relationship, an exponential relationship, or any other relationship. Further, it is recognized that blanket wafers will exhibit a different charge-removal relationship than patterned wafers.

Trajectory Simulation

As noted above, the process model 602 also receives as input operations/cell parameters 612, which may include process parameters, electrode geometry (i.e., the geometry of the various electrodes 402 which make up the electrode assembly 209 as illustrated in FIG. 4), and polishing article construction. In general, the operations/cell parameters 612 are those parameters necessary to simulate a trajectory of points on a wafer. For each point of the wafer, the amount of time affected by each of the electrodes of the electrode assembly 209 can be calculated. In one aspect, a point is affected by an electrode while in direct facing relationship with the electrode via a perforation in the polishing pad (e.g., one of the perforations 205 of the polishing pad 203 shown in FIGS. 2A-B. However, the presence of a contact element on the polishing pad (e.g. one of the contact element 304 shown in FIG. 3) may interfere with the interaction between electrode/zone and the point on the wafer. Hence, a point is considered to be affected by an electrode when the electrode is "visible" from the perspective of the point via a perforation.

Figure 14:
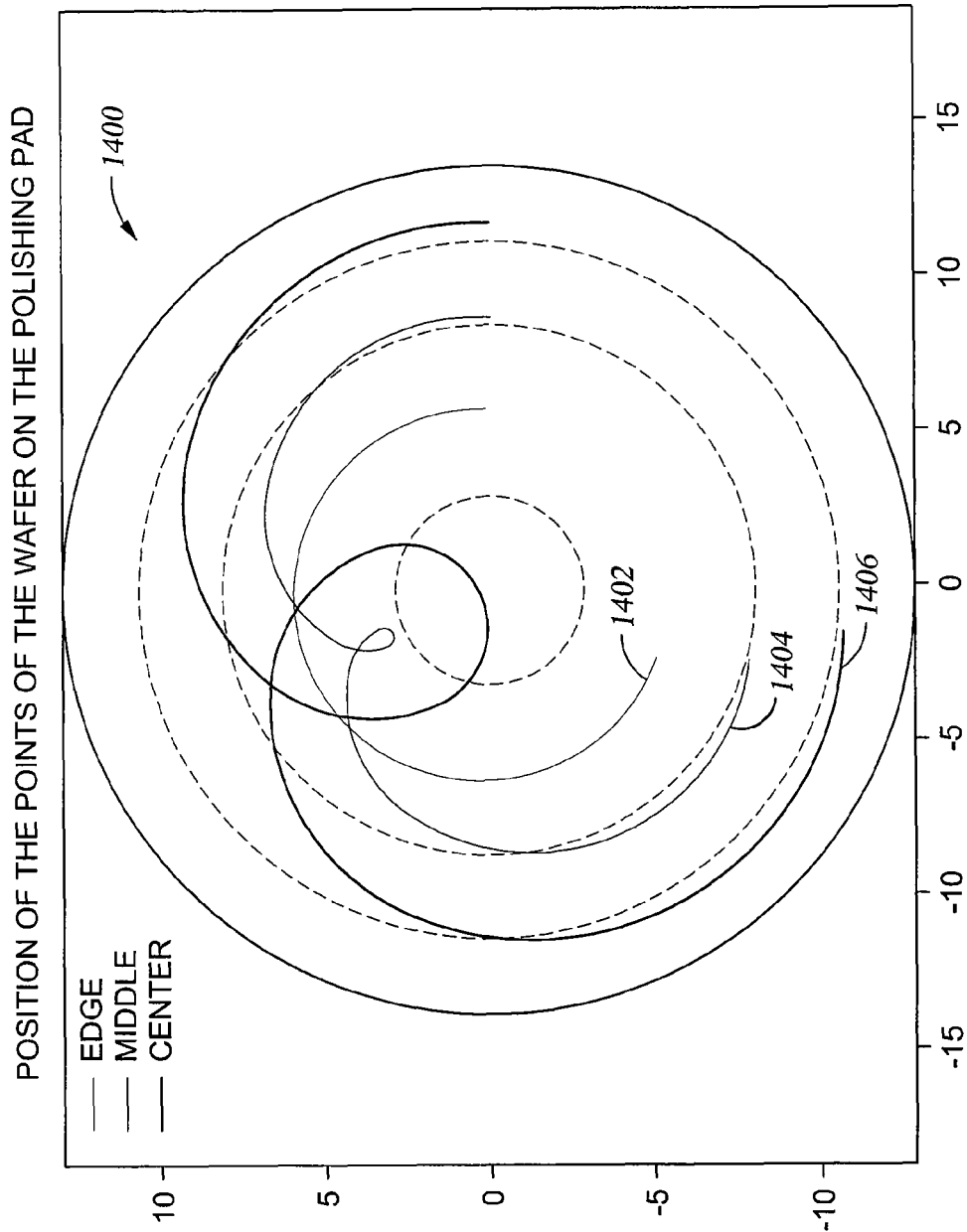
FIG. 14 are representative traces of wafer point trajectories relative to electrode zones.

Referring now to FIG. 14, one illustration of simulated point trajectories is shown. Specifically, FIG. 14 shows the electrode assembly 209 (FIG. 4) and three traces that represent the trajectories of three separate points on a wafer. Only three points are shown for simplicity. In practice, however, the trajectories for a plurality of points would be measured. A first trace 1402 corresponds to a center point on the wafer, a second trace 1404 corresponds to a middle point on the wafer and a third trace 1406 corresponds to an edge point on the wafer. The traces are computer-generated according to a simulation based on the shape of the zones and the relative movement between the wafer and the zones. In addition to the actual path of a wafer point relative to the electrode zones, the time spent affected by each zone is determined according to the simulation by accounting for the relative rotation speeds of the platen and head, the sweep range and frequency and the location of obstructions (e.g., contact element) between the wafer points and the electrodes. The fraction of time spent by a point, j, in front of a counter-electrode, i, is denoted $p_{ij}$.

Figure 15:
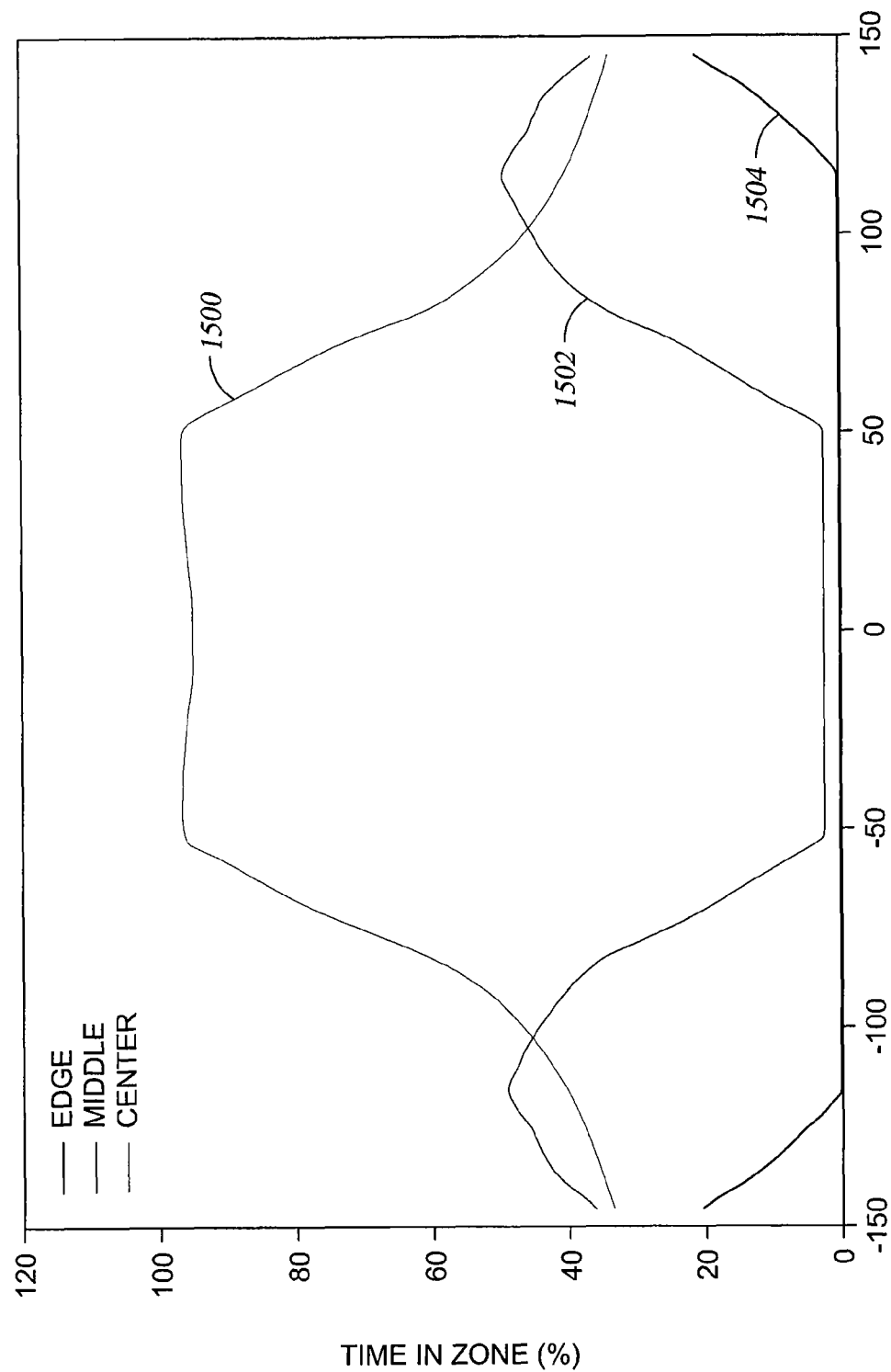
FIG. 15 are representative curves illustrating the percent of time various points on a wafer spent in three separate electrode zones.

One graphical representation of the time spent in the various zones is given in FIG. 15. In particular, three curves represent the time spent by various points on a diameter of the wafer in three separate zones: a central zone, a middle zone, and an edge zone. The zones were defined by concentric electrodes arranged similarly to those shown in FIG. 4. The wafer points are represented on the x-axis (in this illustration the wafer was a 300 mm wafer) and the percent of the total time a point spent in a given zone is represented on the y-axis. A first curve 1500 represents the time wafer points spent in the central zone, a second curve 1502 represents the time wafer points spent in the middle zone and a third curve 1504 represents the time wafer points spent in the edge zone. Note that although points in a central part of the wafer (e.g., between about −50 mm and +50 mm) may spend their entire time in the center zone, the first curve (corresponding to the center zone) does not reach 100 percent. This characteristic is due to obstructions to the points' view of the electrode which defines the center zone. As noted above, a point may only experience a bias when disposed over a perforation in the polishing pad, thereby giving the point a view to the electrode. Further, a point's view may be periodically obstructed by a contact element on the polishing pad.

Process Model Generation

The empirically determined charge-removal relationship and the trajectory simulation are combined to relate charge in each zone to the removal at each wafer point. Based on the trajectory simulation, the average area of the wafer, $A_i$, affected by the $i^{th}$ counter-electrode can be determined. Assuming that the current density is uniform across a zone, i.e., that the voltage drop across the wafer is negligible, the charge-removal relationship in any given zone, $R_i$, can be computed as follows:

$$R_i = a*A_W/A_i*C_i + b \qquad \text{(Equation 1)}$$

In Equation 1, a is the slope (the mathematical expression of the relationship between charge and removal), $A_W$ is the plated area of the wafer, $C_i$ is the charge of the $i^{th}$ electrode and b is the intercept of the mathematical expression of the relationship between charge and removal.

The removal at each point becomes the average of the removal of each zone weighted by the amount of time the point spent in front of each zone, as given by:

$$R_j = \text{sum}(i)(p_{ij}R_i) \qquad \text{(Equation 2)}$$

The process model described above can be summarized in the form of a transfer function taking as input the charge in each zone, C, and generating as output the removal profile R (i.e., the profile of the material to be removed). The charge in each zone, C, is represented by a vector with N components, where N is the number of zones. The removal profile, R, is represented by a vector with n components, where n is the number of sample points chosen on the wafer. Based on the process model described above, the transfer function is essentially linear and can be written as:

$$R = AC + B, \qquad \text{(Equation 3)}$$

where A is a n×N matrix and $A_{ij} = p_{ij}(a*A_W*A_i)$, and B is a (n×1) vector and Bi=b. Thus, the transfer function relates the removal profile to the charge per zone (i.e., the charge read on each channel of the power supply).

It is noted that the process model described above is a "physical" model in that the model accounts for physical parameters in a simulation. However, the process model 602 may be generated in a variety of ways. For example, the model 602 may be a statistical model based on calibration wafers (i.e., the best fit based on x charges, where x is the number of zones).

In any case, the process model 602 calculates a target charge per zone. If $P_{in}$ is the incoming profile (provided by the profile measurement station 102) and the $P_{des}$ is the desired profile, the process model 602 can implement an optimization with respect to the achievable profile. In one embodiment the optimization is a least squares interpolation. Although the optimization may not be uniquely described, specific implementations are contemplated. For example, one optimization is to minimize the standard deviation between the final profile, $P_{fin}$, and the desired profile, $P_{des}$. This optimization may be described as: minimize stddev(Pin−(AC+B)−Pdes). Another optimization is to minimize the maximum deviation between Pfin and Pdes. This optimization may be described as minimize maxdevPin−(AC+B)−Pdes). Using such approaches (and others which will be recognized by those skilled in the art) the optimal values for the target charges per zone can be determined prior to processing a wafer. The power supplies for the respective zones are then controlled to ensure that the target charges are reached.

EXAMPLE

A counter-electrode assembly, such as the counter-electrode assembly 209 was divided into five zones: an inner zone, an inner-central zone, a central zone, an outer-central zone and an outer zone (Z1, Z2, Z3, Z4 and Z5) respectively. The zones were arranged in a concentric circular manner similar to the zones depicted for the electrode assembly 209 shown in FIG. 4. Each of the zones was capable of receiving a separate bias with respect to a material layer of a wafer to be polished. One hundred twenty one points, representing a broad sampling of various locations on the material layer were selected. A pre-determined set of instructions (i.e., a polishing program) that encoded a sequence of relative motion between the counter-electrode (as well as the polishing article) and the material layer of a wafer to be processed was provided to a computer (e.g., the computer 106). An algorithm based on the polishing program was used to determine the sequence of relative positions between the material layer and the individual counter-electrodes of the electrode assembly as a function of time throughout the polishing process. The algorithm calculated the location of each point relative to the five zones of the counter-electrodes for each of a total of 2400 instants in time (time steps). The algorithm also calculated the number of time steps each point was associated with each of the five zones (e.g., the number of times the point would be facing or under each of the zones). For a first order approximation, it is assumed that for embodiments in which the process cell comprises a pad, a point on the material layer only experiences a bias when facing a perforation in the pad. It is also assumed that a point does not experience a bias when directly below a contact element on the pad (i.e., when the point's view of an opposing electrode is obscured by a contact element).

Based upon the program to be used to polish the material layer, the algorithm determined that a first point in the center of the material layer was associated with Z2 for 1080 time steps (i.e. 45% of the total number of time steps), associated with Z1, Z3, Z4, Z5 for 0 time steps, and associated with none of the zones (i.e., the point was not under a perforation in the pad and/or the point was under a contact element, and therefore zero bias was experienced by the point) for the remaining 1320 time steps. Therefore, for 45% of time, point A was associated with Z2, and the expected removal would be 0.45× R2, where R2 is the total removal contributed by Z2.

From the algorithm it was further determined that a second point B, away from the center of the material layer) was associated with Z2 for 570 time steps (or 23.75% of the total number of time steps), associated with Z3 for 774 time steps (or 32.35% of the total number of time steps), and associated with no zones for 1056 time steps. The expected removal for point B is therefore given by an average of the removals for Z1, Z2, Z3, Z4, and Z5, weighted by the percentage of the time spent in each zone. Expressed in mathematical terms, the expected removal for point B is given by the mathematical expression, [0.2375×R2]+[0.3235×R3], where R3 is the total removal contributed by Z3.

The algorithm further calculated the expected removal rate for the remainder of the 121 points on the material layer in a similar manner. Specifically, for each point an expected removal rate was calculated as [P1×R1]+[P2×R2]+[P3×R3]+[P4×R4]+[P5×R5]. P1, P2, P3, P4, and P5 are the percentages of time that the particular point was associated with the zones Z1, Z2, Z3, Z4, and Z5 respectively.

The material layer to be polished had a non-uniform initial profile, Pin. A desired removal profile, Rdes, was calculated as Pin−Pdes, where Pdes is the selected desired profile. A least-squares regression was performed to optimize the values for R1, R2, R3, R4, and R5 such that the actual removal profile, Ract, of the material layer after polishing would closely match the desired removal profile, Rdes. The optimal biases to be applied to each of the zones was then determined using a pre-determined (linear) relationship between removal and charge. The resultant removal profile was similar to the desired removal profile.

Breakthrough Detection and Compensation for Endpoint Detection

Since the removal rate of the conductive film being processed is not uniform across the diameter of the substrate, the underlying film becomes exposed through the polished film in disparate locations. For example, during processing of copper layer having a thickness of about 8000 Å at a rate of about 6000 Å per minute, the layer underlying the copper film begins to be exposed when the remaining copper layer is about 2000-1000 Å thick. As the copper (or other conductive film being removed) no longer completely covers the original plated area, the input $A_W$ begins to diminish rapidly as more and more of the underlying layer is exposed. In other words, the value $A_W$ remains a constant until the underlying film begins to break through the conductive layer being process at $time_{(break)}$, at which time, the value $A_W$ and R become variables over time and can be expressed as $A_{W(t)}$ and $R_{(t)}$. Thus, to maintain accurate endpoint control, the target endpoint, herein expressed as a summation of charge R removed from the wafer, $A_{W(t)}$ is substituted for the value $A_W$ in the calculator of $R_{(t)}$ is adjusted to compensate for the actual remaining film area.

By monitoring the film removal process to determine the incidence of breakthrough at $time_{(break)}$, the removal target profile R may be dynamically adjusted to accurately arrive at the process endpoint by determining $A_{W(t)}$ at process times greater than $time_{(break)}$. The value of $A_{W(t)}$ may be provided by empirical data, known correlation to process indicators or metric, or by other means. For example, the remaining area $A_{W(t)}$ may be determined by empirically, and stored in a database for retrieval by the process control unit 112 during processing. In one embodiment, the database for $A_{W(t)}$ may include values for $A_{W(t)}$ correlated to time, current, voltage or other metric which varies with $A_{W(t)}$.

In another embodiment, a metric such as voltage or current may be sensed as indicator or metric indicative of breakthrough and/or $A_{W(t)}$. Since the electro-process is typically driven by holding one of current or voltage constant, fluctuations in the other attribute (e.g., current in a voltage driven process or voltage in a current driven process) which is normally sensed during processing, may be utilized without additional system hardware to detect breakthrough and provide an indicator for appropriate adjustment of the target endpoint.

Figure 16:
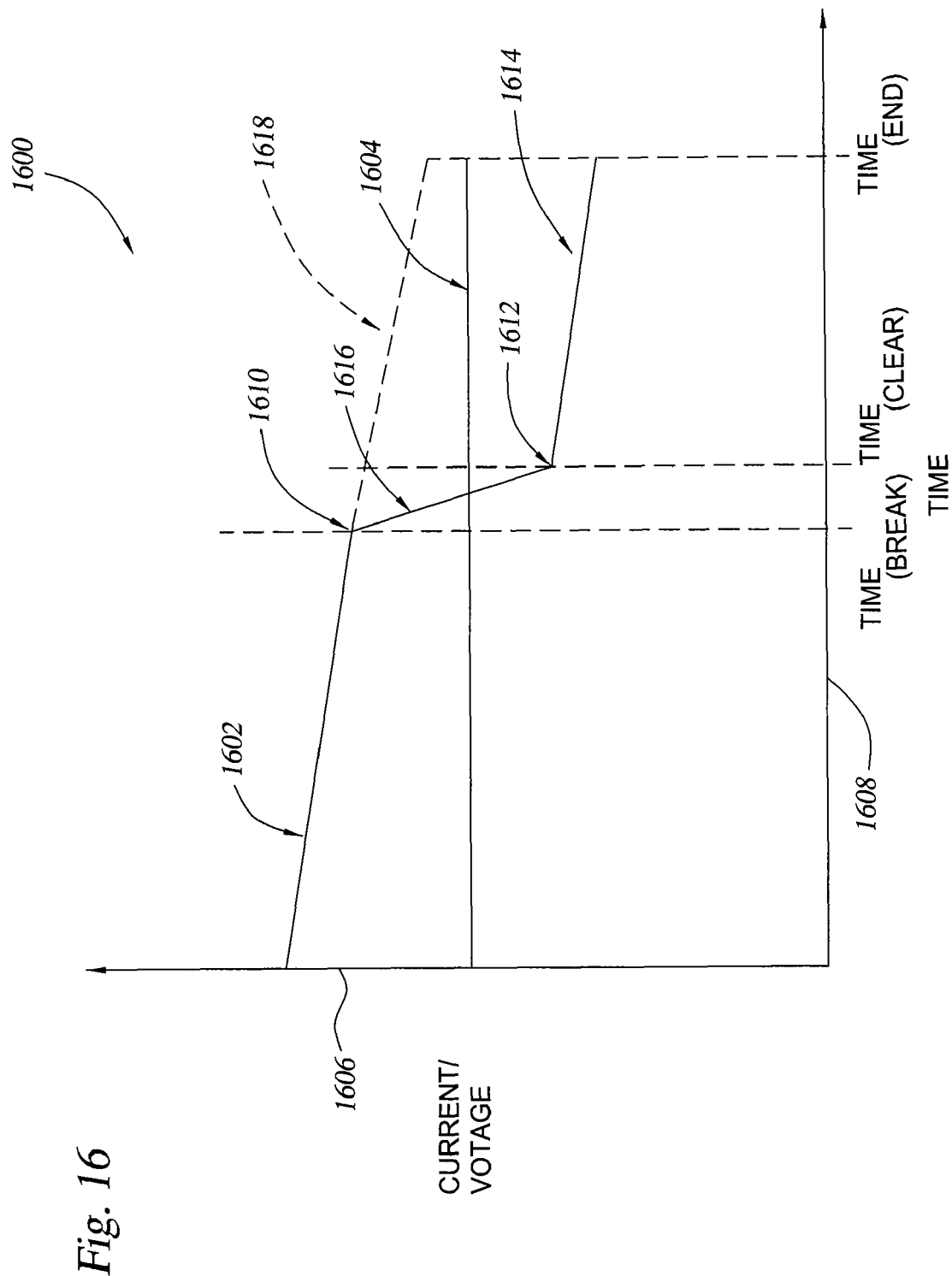
FIG. 16 is a curve plotting voltage and current verse time for an exemplary electro-process.

FIG. 16 depicts a graph 1600 illustrating current 1602 and voltage 1604 traces over an exemplary removal or planarizing process. Amplitude is plotted on the Y-axis 1606 and time plotted on the X-axis 1608. In the embodiment illustrated in FIG. 16, the planarizing process is voltage driven, and as such, the voltage trace 1604 is substantially constant in amplitude until the end of the process at time$_{(end)}$. During the initial portions of the polishing process, the area $A_W$ of the film being removed is substantially constant. At time$_{(break)}$, the layer underlying the film being removed begins to become exposed, and thus, the area of film is now expressed as $A_{W(i)}$. The arrival of the process at time$_{(break)}$ is indicate by a first discontinuity 1610 in the current trace 1602. $A_{W(i)}$ continues to decrease after time$_{(break)}$, and correspondingly causes the current trace 1602 to decrease in response to the increase in sheet resistance of the film being removed as the area of the conductive material decreases. At a time$_{(clear)}$, only the conductive material left in the features, for example, exposed lines and via, are exposed, and thus, the sheet resistance becomes substantially stable again thereby causing the current trance 1602 to become substantially constant in amplitude at a second discontinuity 1612. Time$_{(clear)}$ may be associated with the arrival of the process endpoint, but optionally, an over-polish 1614 period may be utilized to ensure removal of residual material. Typically, the over polish period 1614 is timed, for example, having a 3-10 second duration.

A portion 1616 of the current trace 1604 between the time$_{(break)}$ and time$_{(clear)}$ may be correlated to a theoretical continuation 1618 of the current trace 1602 extending from the trace 1602 at time$_{(break)}$. The continuation 1618 represents the current amplitude which would be present if the conductive layer was removed uniformly until completely gone (e.g., would clear completely from the underlying layer at the same time across the substrate diameter). In one embodiment where features, such as lines, vias and/or other structure, are uniformly distributed across the substrate, the area $A_{W(t)}$ of the remaining conductive layer is proportional to the ratio of the amplitudes of the portion 1616 and continuation 1618 of the current trace 1602 for process times between the time$_{(break)}$ and time$_{(clear)}$. In other embodiments where the features on the substrate do not allow the relation between the portion 1616 and the continuation portion 1618 of the trace to remain linear, the relationship may be calculated or determined empirically.

Thus, once the relationship between the ratio is correlated to the $A_{W(t)}$, $A_{W(t)}$ may be determined by measuring or sensing the current to the electrode during processing. As $A_{W(t)}$ is now available after breakthrough of the conductive layer on the substrate, the target charge profile R for determining the arrival at the process endpoint may be dynamically updated after breakthrough of the conductive material as $R_{(t)}$ by the process control unit 112, such that arrival at the process endpoint is accurately determined.

CONCLUSION

In various embodiments, advantages in electro-processing may be achieved. In some cases, these advantages may be substantial improvements over the prior art. Some of these advantages are now described. However, whether or not an embodiment achieves an advantage and whether or not such an advantage may be considered a substantial improvement is not limiting of the invention. Therefore, the advantages described below do not define or limit the invention, which is limited only by the claims that follow.

In one aspect, calibration requirements are eliminated. Conventionally, thickness measurement is performed by eddy current probes. The eddy current probe measures a current and then correlates the measured value to thickness. In order to ensure accurate measurements the probe must be calibrated for pad wear and changes between different wafer types. Such calibration requirements may be eliminated by some embodiments of the invention. As a result, successful process monitoring and endpoint detection according to embodiments of the invention are independent of pad wear.

In another aspect, good spatial resolution is achieved. Spatial resolution using eddy current probes is limited to the width of the probe (e.g., ¼ inch). Because embodiments of the invention do not rely on such intrusive devices, superior resolution is achieved.

In another aspect, embodiments of the invention are not restricted to wafers having a minimal thickness. In contrast, eddy current probes are limited in their ability to provide accurate measurements for thicknesses less than, for example, 2000 angstroms.

In another aspect, thickness measurements are not corrupted by interference from other metal levels on a wafer. In contrast, adjacent metal levels can interfere with measurements taken by eddy current probes.

While the foregoing is directed to embodiments of the present invention, other and further embodiments of the invention may be devised without departing from the basic scope thereof, and the scope thereof is determined by the claims that follow.

What is claimed is:

1. A method for removing conductive materials from a semiconductor substrate by electro-processing, comprising:
pressing a conductive layer disposed on a substrate in contact with a conductive surface of a polishing pad, wherein the substrate is offset from a center line of the polishing pad;
providing sufficient electrolyte on the polishing pad to establish a conductive path between the conductive layer and an electrode assembly disposed below the polishing pad, the electrode assembly having a plurality of zones that are independently biasable relative to the conductive surface of the polishing pad;
rotating the polishing pad while the substrate is pressed against the conductive surface;
providing electrical bias between the conductive surface and the zones of the electrode assembly;
sensing charge removed from the conductive layer through each zone of the electrode assembly;
determining a time that at least one portion of the substrate is associated with each of the plurality of zones of the electrode to determine the charge removed from each portion of the substrate;

comparing the charge removed from each portion of the substrate to a target charge removed and;

independently controlling bias applied between each zone and the conductive surface in response to the comparison.

2. The method of claim 1 further comprising:
determining a pre-processing profile of the substrate; and
establishing the target for each zone from the pre-processing profile.

3. The method of claim 1, wherein determining the pre-processing profile of the substrate further comprises:
measuring a thickness profile of the substrate prior to polishing.

4. The method of claim 1, wherein providing the electrical bias between the conductive surface and the electrode assembly further comprises:
biasing a first zone of electrode assembly relative a second zone of the electrode assembly.

5. The method of claim 1 further comprising:
sensing a discontinuity in a metric of electro-processing.

6. The method of claim 5, wherein the metric of electro-processing is current passing between an electrode biased relative to the substrate.

7. The method of claim 5, wherein the metric of electro-processing is voltage measured between an electrode and the substrate.

8. The method of claim 5 further comprising:
adjusting the target charge in response to the sensed discontinuity.

9. The method of claim 1, wherein providing the electrical bias between the conductive layer and the electrode assembly further comprises:
biasing an outer zone of the electrode assembly relative to an inner zone of the electrode assembly, wherein the inner and outer zone are concentric.

10. An apparatus for electro-processing, comprising: a platen; an electrode assembly disposed on the platen, the electrode assembly having a plurality of independently biasable concentric zones; a polishing pad disposed on the electrode assembly, the polishing pad having a conductive surface on which substrates are processed; a power source coupled to the conductive surface and the electrode assembly, the power source arranged to electrically bias each zone relative to the conductive surface; a polishing head operable to contact non-concentrically a substrate to the polishing pad; controller arranged to control operation of the power source; and computer readable media, containing instructions which, when executed by the controller, causes the apparatus to perform a polishing operation comprising: rotating the polishing pad while a substrate is pressed against the conductive surface non-concentrically; providing an electrical bias between the conductive layer and zones of the electrode assembly; sensing charge removed from the conductive layer over each zone of the electrode assembly; determining a time that at least one portion of the substrate is associated with each of the plurality of zones of the electrode to determine the charge removed from each portion of the substrate; comparing the charge removed from each portion of the substrate to a target charge removed and; independently controlling bias applied between each zone and the conductive surface in response to the comparison.

11. The apparatus of claim 10, wherein the computer readable media further comprises instructions which causes the polishing operation to further comprise:
adjusting the target endpoint for each zone in-situ.

12. The apparatus of claim 11, wherein the computer readable media further comprises instructions which causes the polishing operation to further comprise:
detecting breakthrough of the conductive layer.

13. The apparatus of claim 11, wherein the computer readable media further comprises instructions which causes the polishing operation to further comprise:
determining an amount of an underlying layer exposed through the conductive layer.

14. The apparatus of claim 10, wherein the conductive surface further comprises:
conductive fillers disposed in a binder.

15. The apparatus of claim 10, wherein the conductive surface further comprises:
a pattern of conductive elements at the center of the polishing pad.

* * * * *